United States Patent
Takayama et al.

(10) Patent No.: US 6,479,260 B1
(45) Date of Patent: Nov. 12, 2002

(54) COLD-INDUCIBLE EXPRESSION VECTOR

(75) Inventors: Masanori Takayama, Otsu (JP); Yoshiko Nomura, Otsu (JP); Ikunoshin Kato, Otsu (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/554,813

(22) PCT Filed: Nov. 17, 1998

(86) PCT No.: PCT/JP98/05171

§ 371 (c)(1),
(2), (4) Date: May 19, 2000

(87) PCT Pub. No.: WO99/27117

PCT Pub. Date: Jun. 3, 1998

(30) Foreign Application Priority Data

Nov. 20, 1997 (JP) ............................................. 9-334792

(51) Int. Cl.[7] ........................... C12P 21/06; C07H 17/00
(52) U.S. Cl. .................... 435/69.1; 435/320.1; 536/23.1
(58) Field of Search .............................. 435/69.1, 320.1; 530/23.1

(56) References Cited

U.S. PATENT DOCUMENTS

| | | | |
|---|---|---|---|
| 5,654,169 A | 8/1997 | Oppenheim et al. | ........ 435/69.1 |
| 5,714,575 A | 2/1998 | Inouye et al. | ................ 530/300 |
| 5,726,039 A | 3/1998 | Oppenheim et al. | ........ 435/69.1 |
| 5,981,280 A | * 11/1999 | Fang et al. | .................. 435/471 |

FOREIGN PATENT DOCUMENTS

WO   WO/98/27220   6/1998

OTHER PUBLICATIONS

Proc. Natl. Acad. Sci. USA vol. 87, pp 283–287, Jan. 1990, Major cold shock protein of *Escherichia coli*.

Journal of Bacteriology, Jun. 1992, p 3867–3873; Identification of the Promoter Region of the *Eschericia coli* Major Cold Shock Gene, cspA.

Molecular Microbiology (1997) 26(2), 321–335; Deletion analysis of cspA of *Escherichia coli*; requirement of the AT-rich UP element for cspA transcription and the downstream box in the coding region for its cold shock induction.

* cited by examiner

*Primary Examiner*—Karen Cochrane Carlson
(74) *Attorney, Agent, or Firm*—MacCord Mason PLLC

(57) ABSTRACT

A vector which is characterized in containing each of the following elements:

(1) a promoter which shows its action in the host to be used;
(2) regulatory region for regulating the action of the promoter of (1); and
(3) a region which codes for the 5'-untranslated region derived from cold-shock protein gene mRNA or a region which codes for the region where substitution, deletion, insertion or addition of at least one base is applied to the said untranslated region.

11 Claims, No Drawings

US 6,479,260 B1

COLD-INDUCIBLE EXPRESSION VECTOR

This application is a national stage application of PCT/JP98/05171, filed Nov. 17, 1998, which claims priority to Japanese application JP334792/99, filed Nov. 20, 1997.

TECHNICAL FIELD OF THE INVENTION

The present invention relates to vector used in a recombinant DNA technique and also to a method for the expression of protein using the said gene.

PRIOR ART

Production of useful proteins using a recombinant DNA technique is a widely-used art at present. Among that, an expression system using *Escherichia coli* as a host is the most commonly used expression system and many proteins have been produced by means of recombinants. It is common for the production of useful proteins by such recombinants to use the so-called expression vector which is constructed by arranging the desired genes under the control of promoter recognized by RNA polymerase. Examples of the promoter used for expression vector are lac, trp, tac, gal and ara when *E. coli*, for example, is used as a host. An example of expression vector utilizing a promoter which is other than that directly recognized by RNA polymerase of *E. coli* is a pET-system (manufactured by Novagen) [*J. Mol. Biol.*, volume 189, pages 113–130 (1986); *Gene*, volume 56, pages 125–135 (1987)] which utilizes a promoter recognized by RNA polymerase of bacteriophage T7 infecting to *E. coli*. In the case of the pET-system, T7RNA polymerase is expressed in *E. coli*, transcription of the desired gene which is arranged at the downstream of T7 promoter on the expression vector by the said T7RNA polymerase takes place and synthesis of the desired protein occurs by means of a translation system of the host.

However, when the desired protein is expressed in a high level in many *E. coli* expression system including the pET-system, it often happens that the desired protein gives an insoluble complex (the so-called inclusion body) and the amount of the desired protein of an active type becomes very small. It has been reported that, in some polypeptides, there are examples where the inclusion body is solubilized and then subjected to a refolding operation to give a polypeptide of an active type. Usually, however, its recovered amount is often low and, in addition, it is necessary to investigate an appropriate refolding condition for each of the desired proteins. Therefore, there has been a demand for a system where the protein of an active type is directly expressed in *E. coli*.

Formation of an inclusion body is believed to take place in such a manner that, during the stage of an intermediate before the translated polypeptide chain is folded to a correct steric configuration, interwinding with other polypeptides takes place due an intermolecular action whereupon a very big insoluble complex is formed. It has been known that, when incubation of a recombinant *E. coli* is carried out at the temperature (20–30° C.) which is lower than the commonly-used temperature of 37° C. in that case, the expressed amount of the protein of an active type increases. That is presumed to be due to the fact that sufficient time is available for folding of the intermediate to a correct structure because of retardation of a translation rate by ribosome and that stability of the expressed protein of an active type increases because of retardation of action of the intracellular protease under a low temperature condition. As such, in the production of protein which is apt to give an inclusion body, a method where a recombinant *E. coli* is incubated at low temperature has been receiving public attention as an effective means.

On the other hand, when the incubating temperature of *E. coli* during a logarithmic growth period is lowered form 37° C. to 10~20° C., growth of *E. coli* once stops and, during that period, expression of a group of proteins called cold-shock proteins is induced. The said proteins are classified into group I (10-fold or higher) and group II (lower than 10-fold) depending upon their inducing levels and examples of the proteins of the group I are CspA, CspB, CspG and CsdA. In the case of CspA among them, its expressed amount after 1.5 hours from the temperature shift of from 37° C. to 10° C. reaches 13% of the total cell protein [*Proc. Natl. Acad. Sci. USA*, volume 87, pages 283–287 (1990)] and, therefore, utilization of promoter of cspA gene for the production of recombinant protein at low temperature has been attempted.

In addition to the above-mentioned advantage of initiation of transcription in a high efficiency at low temperature by a promoter of cspA gene, the following effectiveness has been shown for the recombinant protein expression system under a low temperature condition using the cspA gene.

(1) When a translatable mRNA transcribed from cspA gene does not code for CspA protein having a function or, to be more specific, when it codes for only a part of N-terminal sequence of CspA protein, such an mRNA inhibits the expression of other *E. coli* proteins including the cold-shock protein for long time and, during that period, translation of the said mRNA is carried out preferentially [*J. Bacteriol.*, volume 178, pages 4919–4925 (1996)].

(2) In a position at a 12-base downstream from an initiation codon of cspA gene, there is a sequence called a downstream box consisting of 15 bases and it increases the translation efficiency under a low temperature condition.

(3) A 5'-untranslated region consisting of 159 bases existing at from the initiation point of transcription of cspA gene mRNA to the initiation codon gives a negative influence and a positive influence on the expression of CspA at 37° C. and at low temperature, respectively.

However, although the promoter of the said gene is surely able to initiate the transcription at low temperature in a high efficiency, it actually acts even at the common incubating temperature (37° C.) and it has been suggested that the stability of mRNA transcribed from the said gene regulates the expression of the said gene as well [*Molecular Microbiology*, volume 23, pages 355–364 (1997)]. Therefore, in an expression vector constructed using the promoter of cspA gene, regulation of expression is incomplete and, in case of a gene whose product is harmful to the host, there are some cases where it is difficult to incubate to such an state that *E. coli* containing the expression vector can be induced or even the construction of the expression vector is impossible.

For example, in U.S. Pat. No. 5,654,169, there is a description that, even when β-galactosidase gene which is commonly used for evaluation of promoter is inserted into an expression plasmid using the promoter of cspA gene, it is difficult to keep the constructed product in *E. coli* due to the expressed product.

On the other hand, it has been known that an ability of the promoter of cspA gene to initiate transcription is held at the region which is downstream from −37 from the initiation point of transcription, however, an essential region has not been confirmed yet. Further, the above U.S. Patent shows a region of −40~96 from the initiation point for transcription for the said gene as an essential region for the function as a promoter of cspA gene. However, the said region contains a region of nearly 100 bases which is transcribed to mRNA and, in addition, does not code f or the protein. As such, the minimum region of cspA promoter which is necessary for achieving a transcription having a good efficiency at low temperature has not been clarified yet.

PROBLEMS TO BE SOLVED BY THE INVENTION

Accordingly, an object of the present invention is to offer a vector where a transformant for expression of the said gene can be prepared and where the said gene product can be expressed in a high efficiency even under a low temperature condition even in the case of gene whereby construction of an expression system or efficient production of gene product is difficult in the prior art.

MEANS TO SOLVE THE PROBLEMS

The present inventors have attempted that, in order to achieve the above object, a lac operation sequence is inserted into a downstream of promoter of cspA gene whereby, during the construction of plasmid and incubation until the inducible state, gene expression from the said promoter is regulated. By the use of an expression vector having a cspA promoter which can be regulated by a lac operator constructed as such, there present inventors have succeeded in constructing an endo-sulfated-fucose-containing polysaccharide degrading enzyme (Fdase 2) which has been unable to be constructed with an expression vector utilizing a cspA promoter having no lac operator sequence. The present inventors have further found that, when the lac operator is inactivated during incubation of the transformant which was transformed by the said plasmid and the incubating temperature is made low at the same time, the said enzyme can be induced to expressed. This shows that, as a result of introduction of an operator sequence, construction of a low-temperature expression vector which can regulate the expression at ordinary temperature (37° C.) is now possible.

The present inventors furthermore determined the minimum necessary region of the cspA promoter for being able to maintain its function whereupon they have accomplished the present invention.

The present invention will be summarized as follows. Thus, the first characteristic feature of the present invention relates to vector which is characterized in containing each of the following elements:

(1) a promoter which shows its action in the host to be used;

(2) regulatory region for regulating the action of the promoter of (1); and (3) a region which codes for the 5'-untranslated region derived from cold-shock protein gene mRNA or a region which codes for the region where substitution, deletion, insertion or addition of at least one base is applied to the said untranslated region.

The second characteristic feature of the present invention relates to a method for expression of the desired protein which is characterized in containing the following steps.

(1) a step where a host is transformed by the vector of the first characteristic feature of the present invention wherein a gene coding for the desired protein to be expressed is integrated;

(2) a step where the resulting transformant is incubated; and (3) a step where action of promoter is induced via a function of a regulatory region and, at the same time, incubating temperature is made lower than the ordinary temperature to express the desired protein.

Further, the third characteristic feature of the present invention relates to an isolated cspA promoter which is characterized in containing a base sequence as shown in SEQ ID NO:5 in the Sequence Listing and consisting of a base sequence having 135 or less bases.

BEST MODE FOR CARRYING OUT THE INVENTION

Now the present invention will be illustrated more specifically as hereunder.

There is no particular limitation for the promoter in (1) of the first characteristic feature of the present invention but anything may be used so far as it has an activity of initiating the transcription of RNA in the host used. When such a promoter is used together with a region coding for the 5'-untranslated region derived from the cold-shock protein gene mRNA in the above (3), it can be used as a promoter which responds to low temperature. When a high transcription efficiency is desired during the expression induction, promoter derived from the above-mentioned cold-shock protein gene such as cspA, cspB, cspG, csdA, etc. is suitable for the present invention and, among them, promoter derived from cspA gene is particularly preferred.

With regard to the regulatory region for the above (2), there is no particular limitation so far as it is able to regulate the expression of gene located at the downstream of the promoter of (1). For example, when a region which transcribes an RNA complementary to mRNA transcribed by the promoter (i.e. an antisense RNA) is induced into a vector, translation of the desired protein from the gene located at downstream of the promoter can be inhibited. When transcription of antisense RNA is made under the control of an appropriate promoter which is different from that of (1), expression of the desired protein can be regulated. Alternatively, an operator existing in expression regulatory regions of various genes may be utilized as well. For example, lac operator derived from $E.$ $coli$ lactose operon can be used in the present invention. The function of lac operator can be cancelled by an appropriate inducible substance such as lactose or a substance having a similar structure or, preferably, isopropyl-β-D-thiogalactoside (IPTG) whereby the promoter can be acted thereto. Such an operator sequence is usually arranged near the initiation point for transcription at the downstream of the promoter.

The region coding for the 5'-untranslated region derived from the cold-shock protein mRNA as mentioned in (3) is a region which codes for the area of 5'-side from the initiation codon of mRNA. In the cold-shock protein genes of $E.$ $coli$ (cspA, cspB, cspG and csda), such a region has been characteristically found [$J.$ $Bacteriol.,$ volume 178, pages 4919–4925 (1996); $J.$ $Bacteriol.,$ volume 178, pages 2994–2997 (1996)] and the area of 100 or more bases from the 5'-terminal among the mRNA transcribed from those genes cannot be translated to protein. This region is important for a low temperature dependency of the gene expression and, when the said 5'-untranslated region is added to 5'-terminal of mRNA of any protein, translation from the said mRNA into protein now takes place under a low temperature condition. The 5'-untranslated region derived from the cold-shock protein mRNA may be that where one or more substitution, deletion, insertion or addition is/are applied to the base sequence so far as the function can be maintained.

In the present specification, the term "region" stands for a certain range on nucleic acid (DNA or RNA). The term "5'-untranlated region of mRNA" in the present specification stands for a region that, among the mRNA synthesized by the transcription from DNA, which is present at its 5'-side and does not codes for protein. In the present specification, the said region will be referred to as "5'-UTR" meaning 5'-untranslated region. Incidentally, unless otherwise stipulated, 5'-UTR stands for a 5'-untranslated region of mRNA of cspA gene of *E. coli* or a modified one thereof.

In the vector of the present invention, a region coding for the 5'-UTR derived from the above-listed cold-shock protein gene can be used and that derived from cspA gene can be used particularly appropriately. That where the base sequence is partially modified may be used as well and, for example, that where the base sequence of this region modified by introduction of the operation mentioned in the above (2) can be used as well. As will be shown in the Examples later, it is possible to use a region coding for mRNA containing a base sequence as shown in SEQ ID NO:1 in the Sequence Listing such as the region coding for mRNA of a base sequence as shown in SEQ ID NO:2, NO:3 or NO:4 in the Sequence Listing or, further, to use a region containing the region coding for mRNA wherein such a sequence is modified. The region coding for 5'-UTR of cold-shock protein gene is arranged between a promoter of (1) and an initiation codon of gene coding for the protein to be expressed or an operator may be induced onto the said region. For example, the 5'-UTR of the base sequence as shown by SEQ ID NO:2–4 in the Sequence Listing contains a lac operator sequence in the base sequence and is effective in expression of desired protein which has a selectivity at low temperature.

When a base sequence having a complemnentarity to the anti-downstream box sequence of ribosomal RNA of the host used is contained in the downstream of the 5'-untranslated region in addition to the above constituting elements, the expression efficiency can be increased. In the case of *E. coli* for example, an anti-downstream box sequence is present at the position of 1467–1471 of 16S ribosomal RNA and it is possible to use a region coding for an N-terminal peptide of cold-shock protein containing the base sequence showing a high complementarity with that sequence. For example, a base sequence as shown in SEQ ID NO:28 of the Sequence Listing or a sequence having a high homology with the sequence can be artificially introduced. It is effective that the sequence having a complementarity with the anti-downstream box sequence is arranged in such a manner that it initiates from the place which is about first to fifteenth base from the initiation codon. Gene coding for the desired protein is integrated into vector so that the said protein is expressed as a fused protein with such an N-terminal peptide or that a base substitution(s) is/are introduced by means of a site-directed mutagenesis to make the gene coding for the desired protein has a complementarity with the anti-downstream box sequence. When integration into vector is carried out so as to express the desired protein as a fused protein, the said peptide may be in any length so far as the desired protein does not lose its activity. Vector for expression of such a fused protein may, for example, be that where the connecting part is improved so as to be able to isolate the desired protein from the said fused protein or that where an improvement is done whereby it is expressed as a fused protein and peptide which can be utilized for purification or detection. Further, the vector in which a sequence for completion of transcription (terminator) is arranged at the downstream of the desired protein gene is advantageous for a high expression of the desired protein because of improvement in stability of the vector.

The vector of the present invention may be any vector which has been commonly used such as any of plasmid, phage and virus so far as it can achieve an object as a vector. Further, the region which is other than the above-mentioned constituting elements contained in the vector or the present invention may, for example, contain replication origin, drug-resisting gene used as a selective marker, regulatory gene necessary for functioning as an operator such as lac I$^q$ gene to lac operator, etc. Furthermore, the vector of the present invention may be integrated onto genome DNA of the host after being introduced into a host.

Expression of the desired protein using the vector of the present invention constructed as a plasmid can be carried out according to the following steps for example. Thus, when gene coding for the desired protein is cloned to the plasmid vector of the present invention so that an appropriate host is transformed by the said plasmid, it is possible to obtain a transformant for expressing the said protein. Since an operation of promoter is suppressed by an operator in such a transformant, the above protein is not expressed under a noninducible state and, even if the above protein is toxic to the host, the above vector can be held in the host in a stable manner.

After the above transformant is incubated at an ordinary incubating temperature such as 37° C. under a noninducible state, the action of operator is cancelled to induce a transcription whereby the desired protein is expressed. In that case, when an incubating temperature is made low before or together with the induction of transcription, formation of an inclusion body of the desired protein can be suppressed whereby the desired protein in a form having an activity can be obtained.

The present invention will now be further illustrated by showing the construction of a plasmid vector in a specific manner. Incidentally, in the present specification, *E. coli* CspA protein, region on the gene participating in expression of the said protein and the promoter region of the said gene will be referred to as "CspA", "cspA gene" and "cspA promoter", respectively unless otherwise stipulated. Incidentally, the base sequence for natural cspA gene which has been registered as Accession No. M30139 at GenBank gene database has been laid open is shown as SEQ ID NO:6 of the Sequence Listing. In the said sequence, base numbers 426–430 and 448–453 are core sequences of the promoter; base number 462 is a major initiation point for transcription (+1); base numbers 609–611 are SD sequence (ribosome binding sequence); and base numbers 621–623 and 832–834 are initiation codon and termination codon, respectively, of CspA. Accordingly, that which codes for 5'-UTR in the said sequence is the area of base numbers 462–620.

First, construction of foreign gene expression plasmids as expression plasmids utilizing cspA gene which were prepared by construction of a series of plasmid vector pMM031 (pMM031 and pMM031F1) using cspA gene per se and then foreign gene was introduced therein and expression of protein using the said plasmids will be illustrated.

Detailed method for the construction of such expression plasmids is mentioned in Example 1-(1). For example, plasmid pMM031 has such a structure that a region containing a lac promoter between the AflIII-EcoRI sites of plasmid vector pTV118N (manufactured by Takara Shuzo)

containing ampicillin-resistant gene, replication origin of pUC plasmid, etc. is substituted with a region consisting of a promoter region of cspA gene, a region coding for 5'-UTR and a region coding for an N-terminal part of CspA of 13 amino acid residues. Incidentally, in a plasmid pMM031F1, codon which codes for asparagine which is 13th one from the N-terminal of CspA changes to that which codes for lysine. The promoter regions of cspA gene used for those pMM031 series are the regions at −67 and thereafter counting from the initiation point for transcription of the said gene containing the region necessary for the function. Further, the region coding for the N-terminal 13 amino acid residues of CspA well contains the downstream box sequence playing a high translation efficiency of cspA gene under a low temperature condition. From those reasons, pMM031 series are expression vectors which can well reflect the high protein-expressing efficiency of cspA gene under a low temperature condition.

The fact that the plasmids of pMM031 series function as expression vectors of a low-temperature induction type and are able to express the useful protein as proteins of an active type was confirmed by the use of a reverse transcriptase derived from Rous-associated virus 2 (RAV-2) as an example in Example 1-(2). However, when *E. coli* transformed by a reverse transcriptase-expressing vector constructed by the use of pMM031 series was treated at 37° C., it was observed that, as compared with the transformants of plasmid of pMM031 series containing no foreign gene, the resulting colonies were small and growing rate of the cells was slow as well. This suggests that, when cspA gene (particularly, promoter of the said gene) is utilized, control of expression at 37° C. is insufficient and that is a problem for the production of protein.

It has been shown that the incorrectness of control of expression of cspA gene at 37° C. is so serious that, when the protein to be expressed is far highly toxic to the host, construction of the expression plasmid was impossible. As shown in Example 1-(3), when construction of plasmid which expresses an endo-sulfated-fucose-containing polysaccharide degrading enzyme (Fdase 2) was attempted using a plasmid vector of pMM031 series, construction of the said plasmid was impossible due to the toxicity of the expression product to the host. The fact that the expressed Fdase 2 affected the host whereby construction of the expression vector was impossible can be easily predicted from the fact that, as a by-product during the operation of construction, an open reading frame got out of the position due to deletion of one or two base(s) in the gene coding for the said enzyme whereupon the plasmid which was no longer able to express the said enzyme was obtained. Further, with regard to toxicity of Fdase 2 to the host *E. coli*, it was shown by the fact that no transformant was obtained when the said enzyme-expressing vector was constructed using plasmid pET3d of pET-system (manufactured by Novagen) which was introduced as one of the prior art and then the host *E. coli* BL21 (DE3) for expression having T7RNA polymerase gene was tried to transform.

Now, the present inventors have developed the new expression vectors which are effective in actual use based upon those results and have found the plasmid vector of the present invention.

Thus, the present inventors have developed a low temperature expressing plasmid vector pMM037 which lowers the expression level under the noninducible state (37° C.) and is able to control the expression of the desired protein. The pMM037 has the entirely same structure as pMM01F1 except that a sequence of 31 bases which is designed so as to be able to form a functional lac operator is inserted instead of the region of +2~+18 of downstream of initiation point (+1) for transcription on pMM031F1 of the pMM031 series. Base sequence of the 5'-UTR coded on the plasmid vector pMM037, i.e. that from the initiation point for transcription until the base immediately before the initiation codon for CspA, is shown in SEQ ID NO:2 of the Sequence Listing.

Method for the construction of this expression plasmid vector is mentioned in Example 2-(1). Thus, it is possible to synthesize a primer CSA+1RLAC (base sequence of the said primer is shown in SEQ ID NO:11 of the Sequence Listing) which is designed so as to form a functional lac operator at the downstream of cspA promoter and contains the sequence of the region of upstream of initiation point of transcription of cspA gene and the region of lac operator. When this primer where 5'-terminal is phosphorylated and the primer CSA−67FN (base sequence of the said primer is shown in SEQ ID NO:7 of the Sequence Listing) used for the construction of the plasmid of pMM031 series are used and a PCR is carried out using a plasmid pJJG02 containing a wild type cspA gene [*J. Bacteriol.*, volume 178, pages 4919–4925 (1996)] as a template, DNA fragments being arranged with lac operator region at the downstream of the promoter of cspA gene are able to be obtained. When a restriction enzyme-recognizing sequence is designed near the terminal of the primer used at that time like the NcoI site on the primer CSA−67FN and the NheI site on the primer CSA+1RLAC, construction and modification thereafter are convenient. The resulting DNA fragments are digested with NcoI and inserted between NcoI and SmaI of the plasmid pTV118N (manufactured by Takara Shuzo) whereby a plasmid pMM034 can be constructed.

The resulting pMM034 is cleaved at the NcoI site and the AflIII site on pTV118N, the terminals are made blunt using Klenow fragments and a self-ligation is carried out whereupon a plasmid pMM035 wherefrom lac promoter derived from pTV118N is removed can be constructed.

After that, a sequence coding for a 5'-untranslated region of cspA mRNA at the downstream of the lac operator region of pMM035 can be inserted. Thus, a PCR is carried out using pMM031F1 constructed in Example 1-(1) as a template and using a primer CSA+20FN (base sequence of the primer CSA+20FN is shown in SEQ ID NO:12 in the Sequence Listing) and an M13 primer M4 (manufactured by Takara Shuzo) whereupon it is possible to obtain DNA fragment containing from the 19th base of downstream of the initiation point of transcription of cspA gene to the multi-cloning site of pMM031F1. The DNA fragment is cleaved at the NheI site arranged on CSA+20FN and at the XbaI site on the multi-cloned site and, after that, fragment is inserted between NheI-XbaI of the already-prepared pMM035 in such a direction that each site is regenerated whereupon pMM037 can be constructed.

Ability of control of expression of desired protein at ordinary temperature (37° C.) and efficacy of the expressing ability of the desired protein at low temperature of the resulting plasmid pMM037 can be tested by introducing the gene which codes for the desired protein into a multi-cloning site derived from pTV118N on pMM037.

An expression plasmid having a gene coding for the above-mentioned endo-sulfated-fucose-containing polysaccharide degrading enzyme (Fdase 2) is unable to be even constructed by a plasmid vector of a pMM031 series having no operator. However, the plasmid pMFDA102 which is an expression plasmid constructed by insertion of the said gene into the plasmid vector pMM037 in such a manner that the same open reading frame as in the sequence coding for the N-terminal part of CspA is resulted can be retained in a stable manner in E. coli of a strain which highly expresses the lac repressor such as E. coli JM109. As such, it has been clarified that the above-mentioned plasmid vector has an ability of substantially effective control of expression.

Further, the resulting transformant is incubated at ordinary temperature (37° C.) and, when turbidity suitable for induction is attained, the incubating temperature is made lower such as 15° C. and, at the same time, an appropriate inducing agent such as isopropyl-β-D-thiogalactoside (hereinafter, referred to as IPTG) of a final concentration of 1 mM is added followed by incubating for an appropriate period. The cells obtained from the culture liquid were analyzed for the proteins expressed therein by means of the SDS polyacrylamide gel electrophoresis (SDS-PAGE) to detect the bands of the said fused polypeptide whereby the ability of pMM037 for expressing the desired protein at low temperature can be confirmed. Alternatively, when the resulting cells are subjected to an ultrasonic treatment or the like to prepare a cell extract and a physiological activity of the desired protein contained in the said cell extract is measured, the amount of the desired protein expressed as an active type can be determined. E. coli which was transformed by the above-mentioned plasmid pMFDA102 expressed the active Fdase 2 protein by the above inducing operation.

Incidentally, the cspA promoter still retained an activity of initiating the transcription at low temperature which is inherent function thereto in spite of the fact that, in the construction of the above plasmid vector pMM037, lac operator was introduced into a position (the position of +2 and thereafter) immediately after the initiation point for transcription of the cspA gene. From this fact, it is understood that the cspA promoter retains its function at the region until the initiation point for transcription. Accordingly, for the function of the cspA promoter, the region from the above position of −37 to the initiation point for transcription or, in other words, the area of base numbers 425–461 in the base sequence of the natural cspA gene shown in SEQ ID NO:6 in the Sequence Listing is essential. The base sequence of the essential region for the cspA promoter is shown in SEQ ID NO:5 of the Sequence Listing.

The plasmid vector pMM037 constructed as such can be modified by introduction of changes such as deletion, addition, insertion and substitution of base and the thing where such a change is introduced into the constituting element of the present invention is within a coverage of the present invention as well. As hereunder, examples of the modification of the vector of the present invention using pMM037 as a fundamental structure carried out by the present inventors will be illustrated.

First, a deletion mutation can be introduced into the region coding for 5'-UTR. As mentioned in Example 3-(1), it is possible to construct a plasmid where SD sequence of cspA gene is connected immediately after the lac operator region of pMM037 or, in other words, a plasmid vector pMM036 coding for the 5'-UTR coded on pMM037 as shown in SEQ ID NO:2 of the Sequence Listing where the portion of base numbers 33–161 is deficient. This pMM036 has the entirely same structure as pMM037 except the deletion mutation introduced into a sequence coding for 5'-UTR.

After that, length of the amino acid residues of the N-terminal part of CspA to be fused with the protein to be expressed can be changed. As shown in Example 3-(2), a region coding for the N-terminal part of CspA on pMM037 is used as a total amino acid sequence coding region (70 amino acid residues) and a multi-cloning site is arranged after that whereby it is possible to construct a plasmid vector pMM038 where the desired gene is expressed as a fused polypeptide with 70 amino acid residues of CspA. This pMM038 has the entirely same structure as pMM037 except that the total length of the sequence coding for CspA expressed as a fused polypeptide is contained.

It is also possible to introduce a substitution mutation into a sequence coding for 5'-UTR. As mentioned in Example 3-(3), it is possible to construct a plasmid vector pMM047 where a mutation by substitution with 6 bases is introduced into a region corresponding to +20~+26 counting from the initiation point for transcription of natural cspA gene on the region coding for 5'-UTR on pMM037. This pMM047 has the entirely same structure as the pMM037 except the above substitution mutation. Incidentally, E. coli JM109 transformed by the plasmid vector pMM047 has been named and designated as Escherichia coli JM109/pMM047, deposited as of Oct. 31, 1997 at the National Institute of Bioscience and Human Technology, Ministry of Internal Trade and Industry (1–3, Higashi 1 chome, Tsukubashi, Ibaraki-ken, Japan; post office code: 305–8566) as FERM P-16496 and deposited at the same institute as FERM BP-6523 (date of request for transfer to the international deposition: Sep. 24, 1998). A base sequence of the 5'-UTR coded to the plasmid vector pMM047 or that of from the initiation point for transcription to the base immediately before the initiation codon for CspA is shown in SEQ ID NO:3 of the Sequence Listing.

It is also possible that two or more of such a mutation can be introduced at the same time. As shown in Example 3-(4), it is possible to construct a plasmid vector pMM048 where a deletion mutation of 30 bases is further introduced into a sequence coding for the 5'-UTR of the above plasmid pMM047. This pMM048 has the entirely same structure as the pMM037 except that it contains 6-base substitution same as pMM047 and a deletion of a region corresponding to from +56 to +85 counting from the initiation point for transcription and natural cspA gene or, in the other words, the area coding for the base numbers 70–99 in the base sequence shown in SEQ ID NO:3 of the Sequence Listing. A base sequence of 5'-UTR coded to the plasmid vector pMM048 is shown in SEQ ID NO:4 of the Sequence Listing.

From the fact that the above-mentioned plasmid vectors pMM047 and pMM048 retain the ability of expression of protein at low temperature, it is shown that the mutation introduced into 5'-UTR inherent to cspA gene in the construction of those two genes does not affect the function. Therefore, it is shown that the region on 5'-UTR derived from cspA gene essential for the expression of protein at low temperature is regions of +27~+55 and +86~+159 counted from the initiation point for transcription of natural cspa gene coded on the plasmid pMM048. A base sequence of the said region is shown in SEQ ID NO:1 of the Sequence Listing.

Ability of control of expression of desired protein at ordinary temperature (37° C.) and effectiveness of expressing ability for desired protein at low temperature of modified plasmid vector of pMM037, i.e. pMM036, pMM038, pMM047 and pMM48 can be evaluated, for example, by utilizing β-galactosidase gene (lac Z gene) which is well used for the evaluation of expressing ability of expression vector.

Thus, as mentioned in Example 3-(5), DNA fragments of about 6.2 kbp containing lac Z gene obtained from a plasmid pKM005 [Experimental Manipulation of Gene Expression, pages 15–32, edited by M. Inouye, published by Academic Press, New York, 1983] are inserted into plasmid vector pMM037 and modified plasmids thereof whereupon it is possible to construct a fused β-galactosidase expression vector in which 12 amino acid residues at the N-terminal of CspA and 10 amino acid residues derived from the multi-cloning site are connected at the tenth amino acid residue of β-galactosidase. In the case of pMM038, 70 amino acid residues at N-terminal of CspA and 9 amino acid residues derived from the multi-cloning site code for a fused β-galactosidase connected at the tenth amino acid residue of β-galactosidase. The resulting plasmids containing lac Z gene are named plasmid pMM037lac, pMM036lac, pMM038lac, pMM047lac and pMM048lac, respectively.

E. coli JM109 transformed by each of the plasmids is incubated at ordinary temperature (37° C.) and, when the turbidity suitable for induction is available, the incubating temperature is lowered to 15° C. for example and, at the same time, an appropriate inducing agent such as IPTG of a final concentration of 1 mM is added, then incubation is further conducted for an appropriate period and the β-galactosidase activity in the resulting incubated solution is measured whereby the ability for expressing the protein at low temperature can be compared. When the cells just before the induction is used, the expressed amount at the noninducible state at 37° C. can be compared as well.

The β-galactosidase activity can be measured by a method described in "Experiments in Molecular Genetics", pages 352–355, edited by J. H. Miller and published by Cold Spring Harbor Laboratory in 1972.

As shown in Table 1, the β-galactosidase activity at 37° C. of E. coli transformed by any of the plasmids has the same level as in pTV118Nlac where lac Z gene is introduced into the downstream of lac promoter used as a control and it is now understood that the expression at 37° C. is effectively controlled. Incidentally, the β-galactosidase activity at 37° C. detected at that time is in such a level that is somewhat induced by lactose, etc. contaminated in LB medium (1% trypton, 0.5% yeast extract and 0.5% NaCl; pH 7.0) used for the incubation.

On the other hand, in E. coli transformed by any of the plasmids, an increase in the β-galactosidase activity was noted by a temperature shift to 15° C. and by addition of an inducing agent. This shows that each plasmid has an ability of high expression of the desired protein at low temperature. Incidentally, in the case of the plasmid pMM036 where most of 5'-UTR derived from cspA gene mRNA is lost, the expressing amount of β-galactosidase is low as compared with other plasmids.

Further, the results obtained for pMM047lac and pMM048lac show that the mutation introduced into 5'-UTR of mRNA for which those plasmids code does not badly affect the expression of protein at low temperature or that the region where those mutation is not introduced whose base sequence is shown in SEQ ID NO:1 of the Sequence Listing is essential for its function.

Furthermore, the expressing amount of β-galactosidase at each temperature for the transformants which were transformed by those plasmids was tested and it was found that all of plasmids pMM038lac, pMM037lac and pMM047lac at the temperature of as low as 10° C. or 15° C. showed higher expressing amount, those at the temperature of 20° C. showed the expressing amount of the same level and those at the temperature of 37° C. showed the lower expressing amount as compared with the pTV118Nlac (a control). The result shows that the 5'UTR of mRNA for which those plasmids code is effective for the expression of protein at the temperature state of mostly as low as 15° C. and lower. On the other hand, the plasmid pMM048lac showed the higher expressing amount at the temperature state of as low as 20° C. or lower and showed the similar expressing amount even at 37° C. as compared with pTV118Nlac. This shows that, as a result of mutation caused by introduction into pMM048, the said plasmid acquired a high ability for expression of protein both at ordinary and low temperatures.

On the other hand, it goes without saying that, in the vector of the present invention, the region which is other than the constituting element of the present invention is able to have various functions. For example, the vector of the present invention may contain a multi-cloning site substantially containing no termination codon and a transcription terminator for stabilization of plasmid. As mentioned in Example 4, it is possible to construct a series of vectors having each different open reading frame on a multi-cloning site where the site containing an initiation codon of cspA gene is converted to NcoI site or NdeI site, a multi-cloning site connecting to the region coding for the N-terminal of CspA is changed to a sequence containing substantially no termination codon, the downstream thereof has a sequence wherein termination codon appears in any of the three open reading frames and the further downstream thereof contains a transcription terminator region derived from cspA gene. A plasmid containing pMM047 as a fundamental skeleton is named pCold01NC series (including NcoI site) or pCold01ND series (including NdeI site) plasmid while a plasmid containing pMM048 as a fundamental skeleton is named pCold02NC series or pCold02ND series plasmid. In such a series of plasmids having a multi-cloning site where substantially no termination codon is contained and each open reading frame is different, insertion of foreign gene is easy whereby an expression vector can be easily constructed.

The fact that those pCold01 series and pCold02 series plasmids have similar expressing abilities as their fundamental skeletons, i.e. plasmid pMM047 and pMM048, respectively can be evaluated by utilizing lac Z gene. As shown in Table 5, E. Coli transformed by a plasmid which is prepared by an insertion of lac Z gene into the already-mentioned plasmid shows the similar β-galactosidase expressing pattern as E. coli transformed by pMM047lac or pMM048lac shown in Table 1, respectively and it is shown that the above-mentioned plasmid retains the similar expressing ability as the plasmid pMM047 or pMM048, respectively.

Since all of the vectors of the present invention which are specifically exemplified hereinabove use lac operator as an operator, it is necessary to use a strain of E. coli expressing high amount of lac repressor (lac $I^q$ strain) such as E. coli JM109 when expression of gene is an object. Other operators may be used for the vector of the present invention and, in that case, it is a matter of course that a control method suitable for the said operator is used. Further, as being obvious for the persons skilled in the art, even when lac operator is used as in the case of the above pCold series plasmid, limitation for the host can be made nil by introduction of lac repressor gene (lac I gene) onto this plasmid.

For example, as mentioned in Example 5, it is possible to construct pCold03 series and pCold04 series containing lac I gene. Each of those plasmids has the entirely same structure as pCold01 series and pCold02 series, respectively except that lac I gene is contained therein. It is also possible to similarly construct a plasmid using lac $I^q$ gene, which is a gene expressing a high amount of lac repressor instead of lac I gene, such as pCold05 series and pCold06 series plasmids.

Ability of control of expression of desired protein of the plasmids containing lac I gene or lac I$^q$ gene constructed as such and also effectiveness of ability of expression of desired protein at low temperature thereof can be easily evaluated by insertion of lac Z gene into those plasmids and by the use of *E. coli* DH5 α having no lac I gene as a host. Table 6 shows the effect of lac I and lac I$^q$ genes. At 37° C. which is a noninducible state, expression is not fully controlled in the case of pCold01NC2lac having no lac I gene and a high β-galactosidase activity is noted. Incidentally, in the case of pCold02 (a derivative of pMM048) having higher expressing ability than pCold01 at 37° C., no transformant is obtained using *E. coli* DH5 α as a host. On the contrary, in the case of pCold03NC2lac and pCold04NC2lac having lac I gene, expression at 37° C. is effectively controlled and, further, in the case of pCold05NC2lac and pCold06NC2lac where lac I$^q$ gene is present, expression is more effectively suppressed whereby an effective control is found to be achieved. In addition, in those plasmids, there is no substantial change in terms of an expressing ability for desired protein in an inducible state. Therefore, it is shown that, when lac I gene or lac I$^q$ gene is introduced into the vector of the present invention containing lac operator as a constituting element, there is no limitation for the host whether or not there is lac repressor.

It is also possible that, in order to improve the expression efficiency of the desired gene, a base sequence (downstream box sequence) having a high complementarity to anti-downstream box sequence existing in 16S ribosomal RNA is introduced into the vector of the present invention. The downstream box sequence existing in the region which codes for the N-terminal part of *E. coli* CspA has only 67% of complementarity to the above-mentioned anti-downstream box sequence. When this is made into a base sequence having higher complementarity or preferably 80% or more complementarity, it is possible that the gene which is connected in its downstream is expressed in higher efficiency.

Further, a base sequence coding for a tag sequence which is a peptide for making the purification of the expressed desired gene product easier or a protease-recognizing amino acid sequence utilizable for removal of an excessive peptide in the desired gene product such as a tag sequence can be introduced into the vector of the present invention.

With regard to a tag sequence for the purification, histidine tag consisting of several histidine residues, maltose-bonded protein, glutathione-S-transferase, etc. may be used. Protein to which histidine tag is added can be easily purified using a chelating column and, with regard to other tags, they may be also easily purified using a ligand having a specific affinity with them. Examples of the protease which is utilized for removal of an excessive peptide are factor Xa, thrombine and enterokinase and it is possible to introduce a base sequence coding for amino acid sequence which is specifically cleaved by those proteases into the vector of the present invention.

For example, in Example 6, plasmid (pCold07 series and pCold08 series) into which a downstream box sequence which is completely complementary to anti-downstream sequence existing in 16S ribosomal RNA and a base sequence coding for a recognition amino acid sequence of factor Xa and histidine tag consisting of six histidine residues are introduced are mentioned. When the protein expressing ability of the said plasmid is evaluated using lac Z gene, it is shown that the expressed β-galactosidase activity significantly increases as compared with a plasmid having a downstream box sequence exhibiting a low complementarity. In addition, although the expressed amount of β-galactosidase before induction more or less increases, that is within an allowable level and, as mentioned above, that can be effectively suppressed by changing the lac I gene on those plasmids to lac I$^q$ gene.

When pCold07 series or pCold08 series are used, the desired protein is expressed as a fused protein with a peptide coded to a downstream box sequence, histidine tag and a leader peptide containing recognition amino acid sequence of factor Xa. Since the fused protein contains histidine tag, it can be purified using a chelating column by a single step. After that, the said protein is treated with a factor Xa to cleave the leader peptide from the desired protein and then passed through a chelating column once again whereupon only desired protein wherefrom the leader peptide is removed can be obtained.

EXAMPLES

The present invention will now be further illustrated by way of the following examples although the present invention is not limited thereto.

Among the operations mentioned in this specification, fundamental operations such as preparation of plasmid and digestion with restriction enzyme were carried out according to the methods described in "Molecular Cloning: A Laboratory Manual", 2nd Edition, edited by T. Maniatis, et al., published by Cold Spring Harbor Laboratory, 1989. Further, in constructing the following plasmids, *E. coli* JM109 was used as a host and an aerobic incubation was carried out at 37° C. using LB medium (1% trypsin, 0.5% yeast and 0.5% NaCl; pH 7.0) containing 100 µg/ml of ampicillin or LB medium which was solidified by adding 1.5% of agar thereto unless otherwise mentioned.

Example 1

Construction of Low-temperature Inducible Vector of pMM031 Series and Investigation of Inducing Ability (1) Construction of plasmid vectors pMM031 and pMM031F1.

A PCR was carried out using a plasmid pJJG02 containing cspA gene [*J. Bacteriol.*, volume 178, pages 4919–4925 (1996)] as a template and using synthetic primers CSA-67FN and CSA13R (base sequences of the primers CSA-67FN and CSA13R are given in SEQ ID NO:7 and NO:8, respectively, of the Sequence Listing) to give DNA fragments containing up to the region coding for the 13th amino acid residue from a promoter of cspA gene. The DNA fragments were cleaved at NcoI and EcoRI sites arranged on each of the above-mentioned primers and then inserted into the area between NcoI and EcoRI of a plasmid pTV118N (manufactured by Takara Shuzo) to construct a plasmid pMM030. After that, the said plasmid was digested with NcoI (manufactured by Takara Shuzo) and AflIII (manufactured by NEB), the terminal was made blunt using Klenow fragment (manufactured by Takara Shuzo) and a self-ligation was carried out to give a plasmid pMM031 wherefrom lac promoter derived from pTV118N was removed. The plasmid pMM031 is a plasmid vector having a multi-cloning site of EcoRI-HindIII derived from pTV118N at the downstream of the promoter region (67 bases) of cspA gene, 5'-untranslated region (159 bases) and the region (39 bases) coding for from the N-terminal of CspA to the 13th amino acid residue.

After that, in order to shift the open reading frame starting from the initiation codon of cspA gene on pMM031 onto the multi-cloning site, a plasmid vector pMM031F1 where one base was deleted from the 3'-terminal of the region coding for the N-terminal part of CspA inserted into pMM031 was constructed. The plasmid pMM031F1 was constructed by the entirely same method as in the construction of pMM031 except that a primer CSA13R2 (a base sequence of the primer CSA13R2 is shown in SEQ ID NO:9 of the Sequence Listing) was used instead of primer CSA13R. Accordingly, the resulting plasmid has the same structure as pMM031 except that the 3'-terminal has one less base in the coding region of the N-terminal region of CspA on pMM031. Incidentally, due to such a deletion of one base, the 13th amino acid residue from the N-terminal of CspA coded to the said plasmid pMM031F1 was changed from asparagine to lysine.

(2) Investigation of inducing ability of low-temperature inducible vector of pMM031 series using the gene coding for the reverse transcriptase derived from Rous-associated virus 2 (RAV-2).

A plasmid pT8RAV containing the gene coding for a reverse transcriptase derived from Rous-associated virus 2 (RAV-2) was prepared from *Escherichia coli* JM109/pT8RAV (FERM P-13716) described in the Japanese Laid-Open Patent Hei-07/039,378. The said plasmid was digested with EcoRI and SalI (both manufactured by Takara Shuzo) to give the gene coding for the above reverse transcriptase and DNA fragments containing a transcription termination sequence at the downstream thereof. The DNA fragment was inserted into the area between EcoRI and SalI of pMM031F1 obtained in (1) to construct a plasmid pMM031RAV.

*E. coli* JM109 (manufactured by Takara Shuzo) was transformed using pMM031RAV and pMM031 to form colonies of each of the transformants on LB plate containing 100 μg/ml of ampicillin whereupon it was noted that the colonies of *E. coli* transformed by pMM031RAV was clearly smaller than the colonies of the transformant by pMM031. Then each of the resulting transformants was inoculated on LB medium containing 100 μg/ml of ampicillin and aerobically incubated for one night at 37° C. Each two tubes of the incubated liquid were inoculated on 5 ml of the freshly-prepared same medium at the concentration of 1%, aerobically incubated at 37° C. and, when turbidity became OD600=0.6, the incubating temperature of one of them was made 15° C. and incubation was carried out for 20 hours more. During the incubation, the incubating time needed for arriving the induced turbidity of the transformant by pMM031RAV was about twice of the case of the transformant by pMM031. After completion of the incubation, the incubated liquid was centrifuged to collect the cells and the cells were analyzed by means of an SDS polyacrylamide gel electrophoresis. The result was that, only in the transformant by pMM031RAV incubated at 15° C., a band presumed to be a reverse transcriptase of molecular weight of about 100,000 was noted whereby it was confirmed that the protein expressing system derived from cspA on pMM031 was a low-temperature inducible type.

After that, an extract of *E. coli* was prepared and its reverse transcriptase activity was measured. Thus, *E. coli* JM109 transformed by pMM031RAV was inoculated on LB medium containing 100 μg/ml of ampicillin and aerobically incubated at 37° C. for one night. The culture liquid was inoculated at the concentration of 4% on 100 ml of the same freshly-prepared medium and aerobically incubated at 37° C., the incubating temperature was made 15° C. when the turbidity reached OD600=0.6 and incubation was carried out for 5 hours more. After completion of the incubation, the culture liquid was centrifuged to collect the cells and the cells were suspended in 4.7 ml of a buffer for lysis [50 mM Tris hydrochloride (pH 8.3), 60 mM NaCl, 1 mM EDTA, 1% NP-40, 1 mM DTT and 5 μM 4-aminodiphenylmethanesulfonyl fluoride hydrochloride] to disintegrate the cells by means of the ultrasonic treatment. It was centrifuged and the supernatant liquid was recovered whereupon an extract of *E. coli* was obtained. The extract was diluted to an extent of 10-fold using a diluting solution for enzymes [50 mM Tris hydrochloride (pH 8.3), 10% glycerol, 0.1% NP-40 and 2 mM DTT] and the activity of reverse transcriptase was measured by the method described in the Japanese Laid-Open Patent Hei-07/039,378 whereupon 1061 units of reverse transcriptase activity was detected as a whole. This shows that 10 units of reverse transcriptase activity was expressed per ml of the culture liquid whereby it is now apparent that the expressing amount of pMM031 at low temperature is high.

(3) Cloning of the gene of endo-sulfated-fucose-containing polysaccharide degrading enzyme (Fdase 2) using the low-temperature inducible vector of pMM031 series.

A plasmid was prepared by a conventional method from *E. coli* JM109/pSFDA7; FERM BP-6340) into which a plasmid pSFDA7 containing the gene coding for an endo-sulfated-fucose-containing polysaccharide degrading enzyme (ORF-2; hereinafter, referred to Fdase 2; a base sequence of the gene coding for the said enzyme is shown in SEQ ID NO:10 of the Sequence Listing) derived from Alteromonas species SN-1009. The resulting pSFDA7 was digested with HindIII (manufactured by Takara Shuzo), separated by means of a 1% agarose gel electrophoresis and DNA fragments of about 4.8 kb coding for the C-terminal region of Fdase 2 were cut out, extracted and purified. The DNA fragment was inserted into HindIII site of pMM031 in such a manner that the directions of cspA promoter and Fdase 2 gene were same whereupon pMM031-Fdase 2C was prepared. Then pSFDA7 was digested with SnaBI (manufactured by Takara Shuzo) whereupon DNA fragments of about 2.5 kb containing a region coding for the area from the 4th amino acid residue to C-terminal amino acid of Fdase 2 were isolated. The DNA fragment was inserted into an area between SmaI and SnaBI of the previously prepared pMM031-Fdase 2C and it was attempted to construct a fused polypeptide expressing vector where the 4th amino acid residue and thereafter of Fdase 2 were connected to the same open reading frame as the N-terminal sequence of CspA on pMM031. However, when the plasmids were extracted, purified and analyzed for 26 resulting transformants, it was noted that SnaBI fragments of about 2.5 kb were inserted into 21 plasmids and, only in two of them, the said fragments were inserted in a correct direction. Further, the two plasmids were subjected to analysis for the base sequence of the connected part whereupon it was found that, due to deletion of one base occurred at the cleaved part of SmaI, open reading frames of CspA and Fdase2 were shifted and they were not the plasmids which were able to express the desired fused polypeptide.

In the above construction method, the DNA fragments to be inserted are blunt ends and they are inserted both in normal and reversed directions. Therefore, construction of a fused a polypeptide expressing vector was attempted by other methods. Thus, DNA fragments of about 1 kb which code for about one half of amino acids residues of 4th and thereafter of Fdase 2 obtained by digestion of the plasmid pSFDA7 with SnaBI and XbaI (both manufactured by Takara Shuzo) were isolated. The DNA fragments were inserted into a place between SmaI and XbaI of pMM031-Fdase 2C obtained above whereby construction of the above fused polypeptide expressing plasmid was attempted. However, when plasmids were extracted from the resulting 12 transformants, purified and analyzed, there were only 3 plasmids where the above DNA fragments of about 1 kb were inserted. Further, the result of a base sequence analysis of them taught that deletion of 1–2 base(s) took place at the cleaved part of SmaI as forecasted whereby no plasmid being capable of expressing the desired fused polypeptide was obtained. From the above, it is now apparent that the reason why expression plasmid is not constructed is that, in the case of gene which greatly affects the growth of cells like the expressed product of Fdase 2, function of cspA promoter is not well suppressed at 37° C. whereby the coded genetic product are expressed at the downstream thereof.

Example 2

Construction of Low-temperature Inducible Plasmid Vector pMM037 and Investigation of its Inducing Ability (1) Construction of plasmid vector pMM037

In order to introduce a lac operator region at the downstream of cspA promoter, a primer CSA+1RLAC (a base sequence of the primer CSA+1RLAC is shown in SEQ ID NO:11 of the Sequence Listing) was designed and synthesized. The 5'-terminal of CSA+1RLAC was phosphorylated by Megalabel Kit (manufactured by Takara Shuzo) and a PCR was carried out using plasmid pJJG02 as a template together with the above primer CSA–67FN whereupon DNA fragment in which lac operator region was arranged at the downstream of promoter of cspA gene were obtained. The DNA fragment was digested with NcoI (manufactured by Takara Shuzo) and inserted into an area between NcoI and SmaI sites of a plasmid pTV118N (manufactured by Takara Shuzo) to construct pMM034. The said plasmid was digested with NcoI and AflIII, the terminal was made blunt using Klenow fragment and a self-ligation was carried out to give a plasmid pMM035 wherefrom lac promoter derived from pTV118 was removed.

After that, a PCR was carried out using the plasmid vector pMM031F1 obtained in Example 1-(1) and using primer CSA+20FN (a base sequence of primer CSA+20FN is shown in SEQ ID NO:12 of the Sequence Listing) and M13 primer M4 (manufactured by Takara Shuzo) to give DNA fragment containing from the 19th base at the down stream of the initiation point of transcription of cspA gene on the said plasmid vector to the multi-cloning site of pMM031F1. The DNA fragment was cleaved by NheI site arranged on the primer CSA+20FN and XbaI sited on the multi-cloning site and inserted between the area of NheI and XbaI sites of the previously prepared pMM035 in such a manner that each site was generated whereupon a plasmid vector pMM037 was constructed. This pMM037 is a plasmid having multi-cloning sites of EcoRI-HindIII derived from pTV118N at the downstream of a promoter region (67 bases) of cspA gene, transcription initiation base (one base), 5'-untranslated region (31 bases) derived from lac operator, 5'-unstranslted region (141 bases) derived from cspA and coding region (38 bases) of N-terminal area of CspA. A base sequence of 5'-UTR coded on the plasmid vector pMM037 or the bases from the initiation point of transcription to immediately before the CspA initiation codon is shown in SEQ ID NO:2

(2) Investigation of inducing ability of a low-temperature inducible plasmid vector pMM037 using a gene coding for an endo-sulfated-fucose-containing polysaccharide degrading enzyme (Fdase 2)

Fdase 2 expression plasmid was constructed using a plasmid vector pMM037 by the same manner as in Example 1-(3). Thus, the plasmid pSFDA7 obtained in Example 1-(3) was digested with SnaBI to isolate SnaBI fragment of about 2.5 kb containing a region coding for an area of from the 4th amino acid residue to the C-terminal amino acid of Fdase 2. The DNA fragment was inserted into BamHI site on the plasmid vector pMM037 constructed in (1) which blunt-ended by Klenow fragment whereby it was attempted to construct a fused polypeptide expression vector where the 4th amino acid residue and thereafter of Fdase 2 were connected to the same open reading frame as the N-terminal sequence of CspA on pMM037. Plasmids were extracted from the six resulting transformants, purified and analyzed whereupon it was found that SnaBI fragments of about 2.5 kb were inserted into two of them in a correct direction. When a base sequence of one of them was analyzed, it was confirmed to be a fused polypeptide expression vector where open reading frames of CspA and Fdase2 were same as desired. The plasmid prepared as such was named plasmid pMFDA102.

E. coli JM109 was transformed with pMFDA102 or pMM037. At that time, there was no difference in the size of colonies between the both transformants formed on the plate. Each of the resulting transformants was inoculated in LB medium containing 100 μg/ml of ampicillin and aerobically incubated at 37° C. for one night. Each two tubes of the culture liquid were planted in an amount of 1% each in 5 ml of a freshly prepared same medium, aerobically incubated at 37° C., IPTG was added so as to make its final concentration of 1 mM when the turbidity reached OD600= 0.6 and, after making the incubating temperature of one of them each 15° C., incubation was carried out for 4 hours more. During the incubation, the growth rate of the both transformants before induction was nearly the same. After completion of the incubation, the culture liquid was centrifuged to collect the cells and the cells were suspended in 1 ml of a buffer for lysis of cells [20 mM Tris hydrochloride buffer (pH 7.5), 10 mM $CaCl_2$, 10 mM KCl and 0.3M NaCl] and disintegrated by means of the ultrasonic treatment. They were centrifuged to collect supernatant liquid whereupon E. coli extracts were obtained. The E. coli extracts were analyzed by means of an SDS polyacrylamide gel electrophoresis, a band which was presumably the fused polypeptide of CspA-Fdase 2 having a molecular weight of about 90,000 was observed only in the transformant by pMFDA102 incubated at 15° C. From the above result, it is shown that a low-temperature inducible expression vector capable of constructing expression plasmids was constructed even for the gene such as Fdase 2 where the expression product thereof greatly affected the growth of cells.

Then the degrading activity of the above E. coli extract for an endo-sulfated-fucose-containing polysaccharide was measured by the following operation using the sulfated-fucose-containing polysaccharide-F prepared by the method described in WO 97/26896 as a substrate.

Then 12 μl of 2.5% sulfated-fucose-containing polysaccharide-F solution, 6 μl of 1M $CaCl_2$ solution, 9 μl of 4M NaCl solution, 60 μl of a buffer (pH 7.5) containing 50 mM of acetic acid, imidazole and Tris hydrochloride, 21 μl of water and 12 μl of E. coli extract which was appropriately diluted with the buffer for cell lysis were mixed and the mixture was made to react at 30° C. for 3 hours. The reaction solution was treated at 100° C. for 10 minutes and centrifuged and 100 μl of the resulting supernatant liquid was analyzed by means of an HPLC using a gel filtration column whereby an average molecular weight of the sulfated-fucose-containing polysaccharide-F substrate was compared with that of the reaction product. As controls, a product obtained by the reaction of cell lysis buffer containing no E. coli extract under the same condition and a reaction product by the use of water instead of the sulfated-fucose-containing polysaccharide-F solution were prepared and each of them was similarly analyzed by means of the HPLC.

The amount of the enzyme by which the fucosyl bonds in 1 μmol of the sulfated-fucose-containing polysaccharide-F can be cleaved in one minute is taken as one U. The fucosyl bonds thus cleaved are calculated in accordance with the following equation:

$$\text{Activity(U/ml)} = \{(12 \times 2.5)/(100 \times MF)\} \times \{(MF/M) - 1\} \times \{1/(180 \times 0.01)\} \times 1000$$

| | |
|---|---|
| $(12 \times 2.5)/100 \times MF$ | Sulfated-fucose-containing polysaccharide-F (mg) added to reaction system; |
| MF | Average molecular weight of substrate (sulfated-fucose-containing polysaccharide-F); |
| M | Average molecular weight of reaction product; |
| (MF/M) − 1 | Number of cleavages by enzyme in one molecule of sulfated-fucose-containing polysaccharide-F; |
| 180 | Reaction time (minute); and |
| 0.01 | Volume (ml) of enzyme solution. |

The HPLC is effected under the following conditions:

| | |
|---|---|
| Apparatus | Model L-6200 (manufactured by Hitachi, Ltd.); |
| Column | OHpak SB-806 (8 mm × 300 mm, manufactured by Showa Denko K.K.); |
| Eluent | 25 mM imidazole buffer (pH 8) containing 5 mM of $NaN_3$, 25 mM of $CaCl_2$ and 50 mM of NaCl; |
| Detection | Differential refractometric detector (Shodex RI-71, manufactured by Showa Denko K.K.); |
| Flow rate | 1 ml/minute; |
| Column temperature | 25° C. |

To measure the average molecular weight of the reaction product, marketed pullulan with a known molecular weight (STANDARD P-82, manufactured by Showa Denko K. K.) is analyzed by HPLC under the same conditions as those described above. Then a curve showing the relationship between the molecular weight of the pullulan and the retention time on the OHpak SB-806 is prepared and used as the standard curve for determining the molecular weight of the above-mentioned enzymatic reaction product. The result was that a clear endo-type degrading activity for the sulfated-fucose-containing polysaccharide was detected only in the extract of the transformant by pMFDA102 incubated at 15° C. and that the endo-type degrading activity for sulfated-fucose-containing polysaccharide was 42.6 mU/ml. It was shown from the above that pMM037 was able to express the desired protein in an active type under a low temperature condition.

Example 3
Modification of the Low-temperature Inducible Plasmid Vector pMM037 and Investigation of Inducing Ability (1) Construction of plasmid vector pMM036

A PCR was carried out using plasmid pJJG21 [Mol. Biol., volume 23, pages 355–364 (1997)] containing cspA gene where XbaI site was introduced into the upstream of SD sequence as a template and using primers CSA+20FN and CSA13R2 and the resulting amplified DNA fragment was digested with XbaI and EcoRI (manufactured by Takara Shuzo) to give DNA fragment containing a region coding from the SD sequence to 13th amino acid reside of cspA gene. The DNA fragment was inserted into an area between NheI and EcoRI of the plasmid vector pMM037 obtained in Example 2-(1) to construct a plasmid vector pMM036. This pMM036 has the same structure as the plasmid pMM037 except that a sequence of base numbers 33–161 was deleted from the base sequence coding for 5'-UTR on the plasmid pMM037 shown by SEQ ID NO:2 of the Sequence Listing.

(2) Construction of plasmid vector pMM038

In pMM037, there is a multi-cloning site at the downstream of the coding region (38 bases) of N-terminal region of CspA and the desired gene can be expressed as a fused polypeptide with the N-terminal 12 amino acid residues of CspA. In order to investigate the length of the N-terminal amino acid residue of CspA in the expression of the fused polypeptide, the multi-cloning site was arranged after the whole coding region (70 amino acid residues) of CspA and a plasmid vector pMM038 where the desired gene was able to be expressed in a form of a fused polypeptide with 70 amino acid residues of CspA was constructed. Thus, a PCR was carried out using the above plasmid pJJG02 as a template and using the primers CSA+20FN and CSA70R (a base sequence of the primer CSA70R is shown in SEQ ID NO:13 of the Sequence Listing) to give DNA fragment containing a region coding for the area of from 19th base at the downstream of initiation point for transcription of cspA gene to the 70th amino acid residue on CspA on the said plasmid. The DNA fragment was digested at the NheI and EcoRI sites arranged on each of the primers and then inserted into an area between NheI and EcoRI of the pMM037 obtained in Example 2-(1) to construct a plasmid vector pMM038. This pMM038 was a plasmid vector wherein the region coding for the area from the N-terminal to 13th amino acid residue of CspA on pMM037 was substituted with that which coded for the whole amino acid sequence (70 amino acid residues) of CspA.

(3) Construction of plasmid vector pMM047

In order to introduce 6-base mutation into the region coding for 5'-UTR on the plasmid vector pMM037, primer CSA+27NF1 (a base sequence of the primer CSA+27NF1 is shown in SEQ ID NO:14) was synthesized and then pMM047 was constructed by the same manner as in the construction of pMM037. Thus, a PCR was carried out using the plasmid vector pMM031F1 obtained in Example 1-(1) as a template and using the primer CSA+27NF1 and M13 primer M4 to give amplified DNA fragment. The resulting DNA fragment was digested at NheI site arranged on CSA+27NF1 and also at XbaI site on the multi-cloning site and then inserted into an area between NheI and XbaI of pMM035 obtained in Example 2-(1) in such a direction that each of the sites is regenerated whereupon a plasmid vector pMM047 was constructed. In this pMM047, at the downstream of the part derived from lac operator in the region coding for 5'-UTR on pMM037, base-substituted mutations were introduced at six places. A base sequence of 5'-UTR coded on the plasmid vector pMM047 or that from the initiation point for transcription to the base immediately before the CspA initiation codon is shown in SEQ ID NO:3 of the Sequence Listing.

(4) Construction of plasmid vector pMM048

A plasmid vector pMM048 where mutation by deletion of 30 bases on the sequence coding for 5'-UTR of the plasmid vector pMM047 was constructed. Thus, primers D3F and D3R (base sequences of the primers D3F and D3R are shown in SEQ ID NO:15 and NO:16, respectively, of the Sequence Listing) were designed and synthesized so as to delete the part corresponding to the region of from +56 to +85 at the downstream of the initiation point for transcription of the natural cspA gene existing on pMM047. PCRs were carried out using the plasmid pJJG02 as a template and using each of a combination of primers D3R and CSA+27NF1 and a combination of primers D3F and CSA13R2. The reaction solutions were subjected to the polyacrylamide gel electrophoresis and the amplified DNA fragments separated from primers were extracted from the gel and purified. The resulting amplified DNA fragments were mixed in a PCR buffer, denatured by heating, and cooled gradually to form a hetero double strand. Taq DNA polymerase (manufactured by Takara Shuzo) was added to this mixed solution, the mixture was kept at 72° C. to complete the synthesis of the double strand and then the second PCR was carried out after adding primers CSA+27NF1 and CSA13R2. The resulting amplified DNA fragment was digested at NheI and EcoRI sites arranged on each of the primers and inserted into an area between NheI and EcoRI of the plasmid vector pMM037 obtained in Example 2-(1) to construct a plasmid vector pMM048. This pMM048 was that where, in the region coding for 5'-UTR on pMM047, a part corresponding to the region of +56~+85 counting from the initiation point for transcription in 5'-UTR derived from natural cspA gene was deleted. A base sequence of the 5'-UTR coded on the plasmid pMM048 or that from the initiation point for transcription to immediately before CspA initiation codon is shown in SEQ ID NO:4 of the Sequence Listing.

(5) Investigation of inducing ability of modified low-temperature inducible vector using β-galactosidase gene A plasmid pKM005 containing β-galactosidase (lac Z) gene ["Experimental Manipulation of Gene Expression", pages 15–32, edited by M. Inoue, published by Academic Press, New York, 1983] was digested with BamHI and SalI (both manufactured by Takara Shuzo) and separated by means of 1% agarose gel electrophoresis, and DNA fragment of about 6.2 kb containing lac Z gene was cut out, extracted and purified. The resulting DNA fragment was inserted into an area between BamHI ad SalI of each of the above-mentioned plasmid vectors pMM036, pMM038, pMM047 and pMM048 and the plasmid vector pMM037 obtained in Example 2-(1) and the resulting plasmids were named plasmid pMM036lac, pMM038lac, pMM047lac, MM048lac and pMM037lac, respectively. Except pMM038lac, all of the resulting plasmids code for a fused β-galactosidase where N-terminal 12 amino acid residues and 10 amino acid residues derived from multi-cloning site are connected at the 10th amino acid residue of β-galactosidase. In addition, pMM038lac codes for a fused β-galactosidase where 70 amino acid residues corresponding to full length of CspA and 9 amino acid residue derived from the multi-cloning site are connected at the 10th amino acid residue of β-galactosidase.

On the other hand, construction of a fused β-galactosidase expression vector using pMM031F1 obtained in Example 1-(1) was attempted by the same manner, however, colonies of the resulting transformant were very small and, since the influence of genetic products expressed at 37° C. was believed to be great, further investigation was not carried out. In the meanwhile, as an expression plasmid having other promoter, a plasmid vector pTV118N (manufactured by Takara Shuzo) containing lac promoter-operator was similarly used for the construction of plasmid pTV118Nlac where DNA fragments of about 6.2 kb containing lac Z gene were inserted into an area between BamHI and SalI whereby the inducing ability was compared.

E. coli JM109 was transformed using each of the above plasmids and each of the resulting transformants was inoculated on LB medium containing 100 μg/ml of ampicillin and aerobically incubated at 37° C. for one night. Each of the culture liquid was planted in an amount of 1% on 5 ml of the freshly-prepared same medium, aerobically incubated at 37° C., a part thereof was sampled when the turbidity arrived OD600=0.6~0.8, then IPTG was added to make its final concentration 1 mM and incubation was further carried out at 15° C. The aliquots sampled from each of the cultures incubated at 37° C. just before induction and after 3 hours and 10 hours from the induction were used as a sample for measuring a β-galactosidase activity by the method described in "Experiments in Molecular Genetics", pages 352–355, by J. H. Miller, published by Cold Spring Harbor Laboratory, 1972.

As shown in Table 1, all transformants containing any plasmid expressed the same or even lower β-galactosidase activity as or than pTV118Nlac used as a control at the stage of before induction whereby it is shown that action of cspA promoter of each plasmid is correctly controlled. After induction, in all of transformants containing plasmid except the plasmid pMM036lac, a β-galactosidase activity of 10-fold or more was expressed as compared with those containing pTV118Nlac.

TABLE 1

| plasmid | β-galactosidase activity (Unit) | | |
|---|---|---|---|
| | Before Induction | After 3 hours from Induction | After 10 hours from Induction |
| pMM037lac | 186 | 7707 | 13193 |
| pMM036lac | 242 | 1201 | 3437 |
| pMM038lac | 311 | 17257 | 26203 |
| pMM047lac | 99 | 9263 | 10421 |
| pMM048lac | 472 | 10018 | 23133 |
| pTV118N1ac | 262 | 404 | 1218 |

(6) Evaluation of protein expressing ability at 37° C.

In the transformants prepared in Example 3-(5), those except which were transformed by plasmid pMM037lac were used and their abilities for expression of protein at 37° C. were evaluated. The experiment was carried out by the same operation as in Example 3-(5) except that, as a medium, M9 medium (containing 1 mM MgSO$_4$, 1 mM CaCl$_2$, 0.2% glucose, 0.2% Casamino acid, 0.05 mg/ml tryptophan, 2 μg/ml thiamine and 100 μg/ml ampicillin) was used and, even after addition of IPTG, the incubating temperature was kept at 37° C. The β-galactosidase activities were measured at the two stages of just before the induction and after 2 hours from the induction. The result is shown in Table 2.

The β-galactosidase activity after 2 hours from induction of E. coli transformed by plasmid pMM036lac where most of 5'-UTR was deleted was higher than those containing pMM038lac and pMM047lac unlike the result in Example 3-(5). Between pMM048lac and pTV118Nlac, there was no difference in terms of the activity expressed after the induction. Those facts show that pMM048 is effective for protein expression not only under a low temperature condition but also at 37° C.

TABLE 2

| plasmid | β-galactosidase activity (Unit) | |
|---|---|---|
| | Before Induction | After 2 hours from Induction |
| pMM036lac | 1515 | 24027 |
| pMM038lac | 2695 | 9947 |
| pMM047lac | 894 | 2637 |
| pMM048lac | 4527 | 48547 |
| pTV118N1ac | 5572 | 48051 |

(7) Evaluation of ability for expression of protein at 10° C. and 20° C.

Using the transformants prepared in Example 3-(5) except for the transformant with plasmid pMM036lac, the ability of each transformants for expression of protein was evaluated at 10° C. and 20° C. Experiment was carried out by the same operation as in Example 3-(5) except that the incubating temperature after addition of IPTG was kept at 10° C. or 20° C. The β-galactosidase activities were measured at three stages of 3 hours, 7 hours and 21 hours after the induction in the case of 10° C. while, in the case of 20° C., it was measured at three stages of 1 hour, 3 hours and 7 hours after the induction. The result carried out at 10° C. is shown in Table 3 while that at 20° C. is shown in Table 4.

As shown in Table 3, even the low temperature condition as 10° C., induced expression of far higher β-galactosidase activity than the case containing pTV118Nlac was obserbed in all transformants containing the plasmid whereupon the high expressing ability of those vectors under low temperature condition was confirmed. Among them, pMM038lac shows higher expression amount than the other constructs and shows its particular effectiveness when the desired gene to be introduced into the vector of the present invention is expressed as a fused protein with total coding region of CspA. On the other hand, pMM048lac where the deletion of 30 bases was introduced into 5'-UTR shows the same or a bit higher expression amount compared with pMM047lac having no mutation, indicating that it is effective for protein expression at the temperature condition like 10° C. As shown in Table 4, in the case of pMM047lac under the temperature condition of 20° C., induction expression of lower β-galactosidase activity than the transformants containing other plasmids was noted.

From those experimental results and the induced amount of β-galactosidase activity at 15° C. and 37° C. as shown in Example 3-(5) and Example 3-(6), it is shown that pMM047 is a vector having an expression pattern which is mainly specific to the temperature of as low as 15° C. or lower and that pMM048 where mutation of deletion of 30 bases was introduced into 5'-UTR of pMM047 is a vector which is able to effectively express the desired protein within a temperature range of as broad as from low temperature to ordinary temperature (37° C.).

TABLE 3

(at 10° C.)

| plasmid | β-galactosidase activity (Unit) | | |
|---|---|---|---|
| | After 3 hours from Induction | After 7 hours from Induction | After 21 hours from Induction |
| pMM037lac | 6290 | 10279 | 12066 |
| pMM038lac | 9892 | 28399 | 33209 |
| pMM047lac | 9168 | 12927 | 12098 |
| pMM048lac | 8799 | 13021 | 18547 |
| pTV118N1ac | 905 | 981 | 836 |

TABLE 4

(at 20° C.)

| plasmid | β-galactosidase activity (Unit) | | |
|---|---|---|---|
| | After 1 hour from Induction | After 3 hours from Induction | After 7 hours from Induction |
| pMM037lac | 7737 | 13351 | 27117 |
| pMM038lac | 22840 | 27043 | 34171 |
| pMM047lac | 6881 | 9946 | 12272 |
| pMM048lac | 13423 | 27135 | 58333 |
| pTV118N1ac | 8914 | 22349 | 21238 |

Example 4
Construction of pCold01 and pCold02 Series and Investigation of Their Inducing Ability (1) Construction of pCold01 series plasmid A PCR was carried out using plasmid pJJG02 containing cspA gene as a template and using synthetic DNA primers CSA-tert-FHX and CSA-tert-R (base sequences of the primers CSA-tert-FHX and CSA-ter-R are shown in SEQ ID NO:17 and NO:18, respectively, of Sequence Listing) to give DNA fragment containing the transcription terminator region of cspA gene. The DNA fragment was digested at HindIII and EcoO109I sites arranged on each of the primers and inserted into an area between HindIII located at the end of the multi-cloning site of pMM038 obtained in Example 3-(2) and the EcoO109I site at the downstream thereof whereupon pMM039 was constructed. After that, a synthetic DNA linker prepared by annealing of synthetic oligonucleotides KS-linker 1 and KS-linker 2 (base sequences of KS-linker 1 and KS-linker 2 are shown in SEQ ID NO:19 and NO:20, respectively, of the Sequence Listing) is inserted in an area between KpnI and SalI in the multi-cloning site of pMM039 to construct pMM040.

In the meanwhile, in order to introduce a NcoI site at the translation initiation codon, primers CSA1NC-F and CSA1NC-R (base sequences of CSA1NC-F and CSA1NC-R are shown in SEQ ID NO:21 and NO:22, respectively, of the Sequence Listing) were synthesized. The first PCR was carried out for a combination of the primers CSA1NC-F and CSA70R using plasmid pJJG02 as a template and also for a combination of the primers CSA1NC-R and CSA+17NF1 using plasmid pMM047 as a template. The reaction solution was subjected to 3% agarose gel electrophoresis and the amplified DNA fragments separated from the gel were extracted from the gel and purified. The amplified DNA fragments were mixed in a PCR buffer, denatured by heating, and gradually cooled to form a hetero double strand. Taq DNA polymerase (manufactured by Takara Shuzo) was added to this mixed solution, then the mixture was kept at 72° C. to complete the synthesis of the double strand and the second PCR was carried out using a combination of primers CSA+27NF1 and CSA13R. The resulting amplified DNA fragment was subcloned to pT7Blue T-vector (manufactured by Novagen) to confirm the base sequence and cleaved at NheI and EcoRI sites arranged on each primer and the liberated DNA fragment was inserted into an area between NheI and EcoRI of a plasmid vector pMM040 to construct a plasmid vector pCold01NC1.

Then the second PCR was carried out similarly using primer CSA13R2 or CSA13R3 (a base sequence of the primer CSA13R3 is shown in SEQ ID NO:23 of the Sequence Listing) instead of the primer CSA13R to construct a plasmid vector pCold01NC2 where one base was deleted from the 3'-terminal of the region coding for the N-terminal part of CspA inserted into pCold01NC1 or a plasmid vector pCold01NC3 where one base was added at the terminal, respectively.

These three kinds of plasmid have an NcoI site at the initiation codon of cspA gene on each plasmid and from a series of vectors that the open reading frame starting therefrom is each different on the multi-cloning site. Further, those plasmids have a sequence appearing a termination codon in each of the three open reading frames at the downstream of the multi-cloning site and contain a transcription terminator region derived from cspA gene at further downstream. Incidentally, in pCold01NC2, the 13th amino acid residue from the N-terminal of CspA coded on the said plasmid is changed from asparagine to lysine by deletion of this one base.

Then, pCold01ND series plasmids, pCold01 ND1, ND2 and ND3, where NcoI site at the translation initiation codon of each of pCold01NC series plasmids was substituted with NdeI site, were constructed by the same method that the first PCRs were carried out using primers CSA1ND-F and CSA1ND-R (base sequences of the primers CSA1ND-F and CSA1ND-R are shown in SEQ ID NO:24 and NO:25 of the Sequence Listing) instead of CSA1NC-F and CSA1NC-R, respectively.

The six kinds of pCold01 series plasmids constructed as such have the expression system where pMM047 is a fundamental skeleton, and have the same sequence as pMM047 except for the restriction enzyme site arranged at the initiation codon and for the sequence after the multi-cloning site.

(2) Construction of pCold02 series of vectors

Six kinds of pCold02 series plasmids were constructed by the same method as in Example 4-(1). Thus, in the first PCR using a combination of the primers CSA1NC-R and CSA+ 27NF1 or a combination of the primers CSA1ND-R and CSA+27NF1, a plasmid pMM048 was used as a template instead of a plasmid pMM047 whereupon pCold02 series plasmids, pCold02 NC1, NC2, NC3, ND1, ND2 and ND3 were constructed by the entirely same steps as in Example 4-(1).

The six kinds of pCold02 series plasmids constructed as such have the expression system where pMM048 is a fundamental skeleton and have the same sequence as pMM048 except for the restriction enzyme site arranged at the initiation codon and for the sequence after the multi-cloning site. Further, each of them was as same as the corresponding plasmid of the pCold01 series except the deletion of the part corresponding to the region of +56~+85 from the transcription initiation point in 5'-UTR derived from natural cspA gene which was characteristic to pMM048.

(3) Investigation of inducing ability of pCold01 and pCold02 using β-galactosidase gene An inducing ability of pCold01 and pCold02 was investigated using β-galactosidase by the same method as in Example 3-(5). First, the DNA fragment of about 6.2 kb containing lac Z gene was inserted into an area between BamHI and SalI of pCold01NC2, pCold01ND2, pCold02NC2 and pCold02ND2 and the resulting plasmids were named plasmids pCold01NC2lac, pCold01ND2lac, pCold02NC2lac and pCold02ND2lac, respectively. All of those plasmids code for the fused β-galactosidase where 12 amino acid residues at the N-terminal of CspA and 10 amino acid residues derived from the multi-cloning site are connected at the 10th amino acid residue of β-galactosidase.

E. coli JM109 was transformed with each of the above plasmids and the resulting transformants were subjected to an expression induction experiment at 15° C. by the same operation as in Example 3-(5). The β-galactosidase activities were measured at three stages, i.e. just before induction, 3 hours after induction and 10 hours after induction. The result for pCold01NC2lac and pCold02NC2lac is shown in Table 5. Incidentally, when ND series vectors were used, almost the same inducing ability as in the case of the use of the corresponding NC series vector was shown.

As shown in Table 5, the transformant containing each of the plasmids shows only a low β-galactosidase activity before induction at 37° C. and it is shown that the action of cspA promoter of each plasmid is correctly controlled. After the induction, nearly the same increase in the β-galactosidase activity as that in the case of pMM047lac and pMM048lac as shown in Example 3-(5) was noted, respectively. Accordingly, the pCold plasmid is a series of plasmids having the transcription terminator and multi-cloning site designed for expression of introduced gene and also being able to control the expression at 37° C. whereby the induced gene product can be expressed in a high efficiency under a low temperature condition.

TABLE 5

| plasmid | β-galactosidase activity (Unit) | | |
|---|---|---|---|
| | Before Induction | After 3 hours from Induction | After 10 hours from Induction |
| pCold01NC2lac | 95 | 6819 | 9173 |
| pCold02NC2lac | 256 | 7025 | 13529 |

Example 5

Construction of pCold Series Plasmids, into which lac I Gene is Introduced, and Investigation on the Host (1) Construction of pCold03 series and pCold04 series plasmids pCold01 series and pCold02 series plasmids prepared in Example 4-(1) and Example 4-(2) have no repressor gene on their plasmid vectors and, therefore, it is necessary to use an E. coli strain which is able to highly express lac repressor, as a host. In view of the above, plasmid vectors pCold03 and 04 where lac I gene was introduced into pCold01 and 02 and also plasmid vectors pCold05 and 06 where lac I$^q$ gene was introduced to pCold01 and 02 were constructed, respectively.

Firstly, pMM040 obtained in Example 4-(1) was digested with EcoT22I and the terminals were made blunt using T4 DNA polymerase. DNA fragment containing lac I gene obtained by digestion of pET21b (manufactured by Novagen) with SphI and PshAI (both manufactured by Takara Shuzo) followed by making the terminals blunt using T4 DNA polymerase were inserted thereinto to construct a plasmid wherein the direction of lac I gene was inserted in the reversed direction of the cspA promoter and that was named pMM40I. Similarly, DNA fragment containing lac qgene obtained by digestion of plasmid pMJR1560 [*Gene,* volume 51, pages 225–267 (1987)] with KpnI and PstI (both manufactured by Takara Shuzo) followed by making the termini blunt was introduced into blunt-ended EcoT22I site of pMM040. A plasmid where lac I$^q$ gene was inserted at oposit direction from the direction of cspA promoter was selected and named pMM040I$^q$.

By the use of the same method for construction of pCold01 and 02 described in Example 4-(1) and Example 4-(2), NheI-EcoRI fragment for each series vector was inserted into an area between NheI and EcoRI of pMM040I and pMM040I$^q$ whereupon each six kinds of plasmid vectors of the series pCold03, pCold04, pCold05 and pCold06 were constructed. The pCold03 and pCold04 series plasmids constructed as such have the same structures as pCold01 series and pCold02 series, respectively, except for presence of the lac I gene. Incidentally, pCold05 and pCold06 series plasmids are those where lac I gene in pCold03 and pCold04 series plasmid, respectively, is substituted with the lac I$^q$ gene.

(2) Investigation of the effect of lac repressor using β-galactosidase gene

As same as in Example 3-(5), plasmid pKM005 was digested with BamHI and SalI, and DNA fragment containing the lac Z gene were extracted and purified. The resulting DNA fragment was inserted into an area between BamHI and SalI of NC2 having a fitted frame among the above-mentioned each series of plasmid vectors pCold03, 04, 05 and 06 and the resulting plasmids were named pCold03NC2lac, pCold04NC2lac, pCold05NC2lac, and pCold06NC2lac, respectively.

Transformation of *E. coli* DH5 α strain having no lac repressor (manufactured by Takara Shuzo) was attempted using the six kinds of plasmids, i.e. pCold01NC2lac and pCold02NC2lac constructed in Example 4-(3) and pCold03NC2lac, pCold04NC2lac, pCold05NC2lac, and pCold06NC2lac mentioned hereinabove. At the same time, a transformation was attempted for a plasmid vector pCold01NC2 having no lac Z gene as a control. *E. coli* DH5 α strain was subjected to a transformation by the competent cell method according to the conventional means whereupon, in all the cases of plasmid other than pCold02NC2lac, transformants were obtained in the same transformation efficiency as in the control while no transformant was obtained at all in the case of pCold02NC2lac. Further, in the case of pCold01NC2lac, colonies of the resulting transformant was smaller than those of other transformants.

After that, ability of expression control of each plasmid for desired protein and expression ability for desired protein at low temperature were investigated. Thus, each of the resulting transformants was inoculated in LB medium containing 100 μg/ml of ampicillin and aerobically incubated at 37° C. for one night. The culture liquid was planted in an amount of 2% to 5 ml of the freshly prepared same medium and aerobically incubated at 37° C. When the turbidity of the culture reached OD600=around 0.6, a part thereof was sampled and IPTG was added to make its final concentration 1 mM and an incubation was carried out at an incubating temperature of 15° C. The culture liquids which were sampled from the culture liquid incubated at 37° C. just before the induction and those after 3 hours, 7 hours and 24 hours from the induction were used as samples and subjected to a measurement for a β-galactosidase activity by the same manner as in Example 3-(5).

As shown in Table 6, the transformant having pCold01NC2lac containing no lac I gene shows a high β-galactosidase activity even under the noninducible state at 37° C. while, in the transformants by the other plasmids containing lac I gene or lac I$^q$ gene, low β-galactosidase activities are shown. This shows that the plasmids of the series from pCold03 to pCold06 having lac I or lac ₁q gene on plasmid substantially carry out suppression of expression in an effective manner under the incubating condition at 37° C. That further shows that, at 37° C., expression control is incomplete only by the function of the region coding for 5'-UTR of cspA gene and that, only when the operator sequence arranged on those plasmids normally functions, substantial expression control is achieved. It has been also clarified that the β-galactosidase activity of the transformants of pCold05NC2lac and pCold06NC2lac having lac I$^q$ gene is lower than the transformants of pCold03NC2lac and pCold04NC2lac having lac I gene whereby the lac I$^q$ gene is able to more effectively control the expression.

On the other hand, after the expression induction by addition of the inducing agent and temperature shift to low temperature, increase in β-galactosidase activity with a lapse of time was noted in any of the cases of the transformants by plasmids containing lac I gene or lac ₁q gene. Such inducible levels well coincides with the induction pattern of the transformant of *E. coli* strain highly expressing the lac repressor with pCold01NC2lac or pCold02NC2lac as shown in Table 5 and it shows that, even when lac I gene is arranged on vector, that does not affect the ability of inducing the expression of the desired protein. This means that, in the case of the vector of the present invention where lac operator is used an operator, limitation for the host concerning lac I gene becomes nil when lac I gene or lac I$^q$ gene is introduced on vector.

TABLE 6

| | β-galactosidase activity (Unit) | | | |
|---|---|---|---|---|
| plasmid | Before Induction | After 3 hours from Induction | After 7 hours from Induction | After 24 hours from Induction |
| pCold01NC2lac | 16672 | 12823 | 15866 | 22779 |
| pCold03NC2lac | 109 | 7469 | 9414 | 27055 |
| pCold04NC2lac | 190 | 6860 | 14523 | 45464 |
| pCold05NC2lac | 48 | 3107 | 3985 | 9734 |
| pCold06NC2lac | 52 | 4340 | 9324 | 23161 |
| pCold01NC2 | 16 | 141 | 148 | 72 |

Example 6

Construction and Investigation of the Inducing Ability of Low-temperature Inducible Vectors pCold07 and pCold08 Series Plasmids Having Highly-complementary Downstream Box Sequence and Tag for Purification (1) Construction of plasmids pCold07NC2 and pCold08NC2

In pCold03 series or pCold04 series plasmids, there is the multi-cloning site at the downstream of the N-terminal coding region of CspA and the desired protein is expressed as a fused protein with 12 or 13 amino acid residues of N-terminal of CspA. There is a downstream box sequence in the N-terminal coding region of CspA and, when an anti-downstream box sequence of *E. coli* is thought to be 15 bases of 1467–1481 in 16S ribosomal RNA, this sequence shows a complementarity to such an extent that ten of the said 15 bases are annealed. The base sequence coding for the N-terminal of CspA was substituted with a base sequence as shown in SEQ ID NO:28 of the Sequence Listing completely complementary to the above-mentioned sequence consisting of 15 bases and then a sequence coding for histidine residue of 6 residues as a tag sequence for purification and a base sequence coding for recognition amino acid sequence of protease factor Xa for excising the leader peptide coded by those sequences were introduced into the further downstream thereof whereupon plasmids pCold07NC2 and pCold08NC2 were constructed.

First, a plasmid pCold03NC2 was digested with NcoI and EcoRI to remove a region coding for the N-terminal sequence of cspA gene on pCold03NC2 whereupon vector fragment was prepared. Then synthetic nucleotides DB-3 and DB-4 (base sequences of DB-3 and DB-4 were shown in SEQ ID NO:26 and NO:27 of the Sequence Listing) were synthesized, annealed and inserted into an area between NcoI and EcoRI of the previously-prepared pCold03NC2 to construct plasmid Cold07NC2. In addition, by the entirely same steps, plasmid pCold08NC2 was constructed wherein the region coding for the N-terminal sequence of cspA gene on the plasmid pCold04NC2 was substituted with the said synthetic DNA linker.

(2) Investigation on the inducing ability of the modified type of low-temperature inducible vector using β-galactosidase gene The plasmid vector pCold01NC2lac constructed in Example 4-(3) was digested with BamHI and SalI and DNA fragment of about 6.2 kb containing lac Z gene was extracted and purified. The resulting DNA fragment was inserted into an area between BamHI and SalI of the above-mentioned plasmids pCold07NC2 and pCold08NC2 and the resulting plasmids were named pCold07NC2lac and pCold08NC2lac, respectively. All of those plasmids code for a fused β-galactosidase where an N-terminal leader peptide consisting of 25 amino acid residues in total, which comprises five residues coded by a downstream box sequence which is completely complementary to the anti-downstream box sequence in a 16S ribosomal RNA, six residues of histidine residue as the tag sequence for purification, four amino acid residues which are the amino acid sequence recognized by the factor Xa, and ten amino acid residues derived from the multi-cloning site, is connected to β-galactosidase at the 10th amino acid residue. In the meanwhile, as an expression plasmid having other plasmid, plasmid pET21blac wherein the DNA fragment of about 6.2 kb containing lac Z gene was inserted into an area between BamHI and SalI of pET-system plasmid pET21b (manufactured by Novagen) was constructed and its inducing ability was compared.

E. coli JM109 [E. coli JM109(DE3) manufactured by Promega in the case of pET21blac] was transformed with each of the above-mentioned plasmids and pCold01NC2lac and pCold02NC2lac constructed in Example 4, and the resulting transformants were subjected to an experiment for expression induction at 15° C. by the same operation as in Example 3-(5). The β-galactosidase activity was measured at the three stages of just before induction, 3 hours after induction, and 10 hours after induction.

As shown in Table 7, the transformants containing pCold07NC2lac and pCold08NC2lac showed only low β-galactosidase activities before induction at 37° C. whereby it was shown that the action of cspA promoter of each plasmid was correctly controlled. In addition, after 7 hours from induction, in the case of the transformant containing plasmid pCold07NC2lac, 5-fold or more β-galactosidase activity was expressed as compared with that containing pCold03NC2lac and, in the case of the transformant containing plasmid pCold08NC2lac, 4-fold or more β-galactosidase activity was expressed as compared with that containing pCold04NC2lac. Further, when compared with pET system which is an effective expression vector among the known expression vectors, it was found that pCold07 series and pCold08 series plasmids showed a higher expressing ability especially within a short period after induction at low temperature.

TABLE 7

| plasmid | β-galactosidase activity (Unit) | | |
|---|---|---|---|
| | Before Induction | After 3 hours from Induction | After 7 hours from Induction |
| pCold03NC21ac | 37 | 7253 | 9282 |
| pCold04NC21ac | 230 | 6311 | 12592 |
| pCold07NC21ac | 359 | 31335 | 53069 |
| pCold08NC21ac | 705 | 33863 | 55850 |
| pET21b1ac | 144 | 6103 | 32934 |

Advantages of the Invention

In accordance with the present invention, there is offered an expression vector where expression at ordinary temperature is able to be controlled and a high expression efficacy is achieved under a low temperature condition. By the use of the said vector, it is possible to give a transformant containing the gene coding for protein which shows a harmful action to the host. In addition, when a protein expression is carried out under a low temperature condition utilizing the said vector, formation of an inclusion body is suppressed whereby it is possible to efficiently give a protein having an activity.

Free Text of Sequence Listing

SEQ ID NO:7 shows a base sequence of primer CSA–67FN.

SEQ ID NO:8 shows a base sequence of primer CSA–13R.

SEQ ID NO:9 shows a base sequence of primer CSA–13R2.

SEQ ID NO:11 shows a base sequence of primer CSA+1RLAC.

SEQ ID NO:12 shows a base sequence of primer CSA+20FN.

SEQ ID NO:13 shows a base sequence of primer CSA70R.

SEQ ID NO:14 shows a base sequence of primer CSA+27NF1.

SEQ ID NO:15 shows a base sequence of primer D3F.

SEQ ID NO:16 shows a base sequence of primer D3R.

SEQ ID NO:17 shows a base sequence of primer CSA-ter-FHX.

SEQ ID NO:18 shows a base sequence of primer CSA-ter-R.

SEQ ID NO:19 shows a base sequence of a synthetic oligonucleotide KS-linker 1.

SEQ ID NO:20 shows a base sequence of a synthetic oligonucleotide KS-linker 2.

SEQ ID NO:21 shows a base sequence of primer CSA1NC-F.

SEQ ID NO:22 shows a base sequence of primer CSA1NC-R.

SEQ ID NO:23 shows a base sequence of primer CSA13R3.

SEQ ID NO:24 shows a base sequence of primer CSA1ND-F.

SEQ ID NO:25 shows a base sequence of primer CSA1ND-R.

SEQ ID NO:26 shows a base sequence of a synthetic oligonucleotide DB-3.

SEQ ID NO:27 shows a base sequence of a synthetic oligonucleotide DB-4.

What is claimed is:

1. A vector which is characterized in containing each of the following elements:
   (1) a promoter which shows its action in the host to be used;
   (2) regulatory region for regulating the action of the promoter of (1); and
   (3) a region which codes for the 5'-untranslated region derived from cold-shock protein gene mRNA or a region which codes for the region where substitution, deletion, insertion or addition of at least one base is applied to the said untranslated region and which contains a base sequence as shown in SEQ ID NO:1 in the Sequence Listing.

2. A vector according to claim 1 in which a promoter is a promoter derived from cold-shock protein gene.

3. A vector according to claim 2 in which a promoter derived from cold-shock protein gene is a promoter derived from cspA gene of *E. coli*.

4. A vector according to claim 3 in which a promoter derived from cspA gene of *E. coli* is a promoter containing a base sequence as shown in SEQ ID NO:5 in the Sequence Listing.

5. A vector according to claim 1 in which regulatory region is an operator.

6. A vector according to claim 5 in which an operator is a lac operator.

7. A vector according to claim 1 which contains a region coding for the 5'-untranslated region containing any of base sequences as shown in SEQ ID NO:2–4 in the Sequence Listing.

8. A vector according to claim 1 which further contains, downstream of the 5'-untranslated region, a base sequence having a complementarity to the anti-downstream box sequence of ribosomal RNA of the host used.

9. A vector according to claim 8 which contains, in the downstream of the 5'-untranslated region, a base sequence as shown in SEQ ID NO:28 in the Sequence Listing.

10. An isolated promoter consisting of a base sequence as shown in SEQ ID NO: 5 in the Sequence Listing.

11. An isolated promoter containing a base sequence as shown in SEQ ID NO: 5 in the Sequence Listing and consisting of a base sequence having 135 or less bases, wherein the promoter does not contain the region which is ascribed to mRNA.

* * * * *

```
                        SEQUENCE LISTING

<160> NUMBER OF SEQ ID NOS: 28

<210> SEQ ID NO 1
<211> LENGTH: 103
<212> TYPE: RNA
<213> ORGANISM: Escherichia coli

<400> SEQUENCE: 1
caguguagua aggcaagucc cuucaagagc cuuuaacgcu ucaaaaucug uaaagcacgc      60
cauaucgccg aaaggcacac uuaauuauua aagguaauac acu                      103

<210> SEQ ID NO 2
<211> LENGTH: 173
<212> TYPE: RNA
<213> ORGANISM: Escherichia coli

<400> SEQUENCE: 2
aauugugagc ggauaacaau uugaugugcu agcauuaaag caguguagua aggcaagucc      60
cuucaagagu uaucguugau accccucgua gugcacauuc cuuuaacgcu ucaaaaucug     120
uaaagcacgc cauaucgccg aaaggcacac uuaauuauua aagguaauac acu           173

<210> SEQ ID NO 3
<211> LENGTH: 173
<212> TYPE: RNA
<213> ORGANISM: Escherichia coli

<400> SEQUENCE: 3
aauugugagc ggauaacaau uugaugugcu agcgcauauc caguguagua aggcaagucc      60
cuucaagagu uaucguugau accccucgua gugcacauuc cuuuaacgcu ucaaaaucug     120
uaaagcacgc cauaucgccg aaaggcacac uuaauuauua aagguaauac acu           173

<210> SEQ ID NO 4
<211> LENGTH: 143
<212> TYPE: RNA
<213> ORGANISM: Escherichia coli

<400> SEQUENCE: 4
aauugugagc ggauaacaau uugaugugcu agcgcauauc caguguagua aggcaagucc      60
cuucaagagc cuuuaacgcu ucaaaaucug uaaagcacgc cauaucgccg aaaggcacac     120
uuaauuauua aagguaauac acu                                           143

<210> SEQ ID NO 5
<211> LENGTH: 37
<212> TYPE: DNA
<213> ORGANISM: Escherichia coli

<400> SEQUENCE: 5
ttgcatcacc cgccaatgcg tggcttaatg cacatca                              37
```

<210> SEQ ID NO 6
<211> LENGTH: 1209
<212> TYPE: DNA
<213> ORGANISM: Escherichia coli

<400> SEQUENCE: 6

| | | | | | |
|---|---|---|---|---|---|
| aagcttcgat | gcaattcacg | atcccgcagt | gtgatttgag | gagttttcaa | tggaatataa | 60 |
| agatccaatg | catgagctgt | tgagcagcct | ggaacagatt | gttttttaaag | atgaaacgca | 120 |
| gaaaattacc | ctgacgcaca | gaacaacgtc | ctgtaccgaa | attgagcagt | tacgaaaagg | 180 |
| gacaggatta | aaaatcgatg | atttcgcccg | ggttttgggc | gtatcagtcg | ccatggtaaa | 240 |
| ggaatgggaa | tccagacgcg | tgaagccttc | aagtgccgaa | ctaaaattga | tgcgtttgat | 300 |
| tcaagccaac | ccggcattaa | gtaagcagtt | gatggaatag | acttttatcc | actttattgc | 360 |
| tgtttacggt | cctgatgaca | ggaccgtttt | ccaaccgatt | aatcataaat | atgaaaaata | 420 |
| attgttgcat | cacccgccaa | tgcgtggctt | aatgcacatc | aacggtttga | cgtacagacc | 480 |
| attaaagcag | tgtagtaagg | caagtccctt | caagagttat | cgttgatacc | cctcgtagtg | 540 |
| cacattcctt | taacgcttca | aaatctgtaa | agcacgccat | atcgccgaaa | ggcacactta | 600 |
| attattaaag | gtaatacact | atgtccggta | aaatgactgg | tatcgtaaaa | tggttcaacg | 660 |
| ctgacaaagg | cttcggcttc | atcactcctg | acgatggctc | taaagatgtg | ttcgtacact | 720 |
| tctctgctat | ccagaacgat | ggttacaaat | ctctggacga | aggtcagaaa | gtgtccttca | 780 |
| ccatcgaaag | cggcgctaaa | ggcccggcag | ctggtaacgt | aaccagcctg | taatctctgc | 840 |
| ttaaaagcac | agaatctaag | atccctgcca | tttggcgggg | attttttat | ttgttttcag | 900 |
| gaaataaata | atcgatcgcg | taataaaatc | tattattatt | tttgtgaaga | ataaatttgg | 960 |
| gtgcaatgag | aatgcgcaac | gccgtaagta | aggcgggaat | aatttcccgc | cgaagactct | 1020 |
| tactctttca | atttgcaggc | taaaaacgcc | gccagctcat | aactctcctg | tttaatatgc | 1080 |
| aattcacaca | gtgaatctct | tatcatccag | gtgaaaaata | aaagcgtgaa | acaaatcact | 1140 |
| attaaagaaa | gtaatctata | tttctgcgca | ttccagctct | gtgttgattt | cacgagtatg | 1200 |
| tactgcacc | | | | | | 1209 |

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: primer
      CSA-67FN

<400> SEQUENCE: 7
ccgttccatg gccgattaat cataaatatg                                    30

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: primer
      CSA13R

<400> SEQUENCE: 8
ggaattcgtt gaaccatttt acg                                           23

<210> SEQ ID NO 9

```
<211> LENGTH: 22
<212> TYPE: DNA
<213> ORGANISM: Artificial Sequence
<220> FEATURE:
<223> OTHER INFORMATION: Description of Artificial Sequence: primer
      CSA13R2

<400> SEQUENCE: 9
ggaattcttg aaccatttta cg                                              22

<210> SEQ ID NO 10
<211> LENGTH: 2442
<212> TYPE: DNA
<213> ORGANISM: Alteromonas sp.

<400> SEQUENCE: 10
atgaaaatac gtaatgtttg tcgtagtgcg gtgcttttag cttgatgtc tttaaataca      60 tacgcagaaa caaaagctga ttggatgcaa ggtaactggg ggatcagtta tcgaatacct    120
ggaggagata ttaattactc aggtagtcat gttgcagaat acaatgtaag agccgcagtt    180
gaacaaatct cagcaattcc tggtttgaag tgggtacaaa ttaatttaac caacggtgca    240
tctggtgatc gttttatagt ccctgtaaca gaagttgaag ccattaatcc tttatccgct    300
cctaacagta ttaatgactt atacgatcct actttacctg gcgagatct ttttgagcaa     360 ctggcattag ccttcaaagc taaaggcata agagttgttg cttatattgc gactcaaggg    420
cctggcatgc tcaagcatgg tgctgaaaac tcgatggatg aagatgactc cattactgac    480
tgtaaatcgt ctaagccatt agtaaccgat cttgatacac aagtttactg ttcagcaaat    540
atgaatcgct ggagagatta cgttttagaa caatacccat caaccagtct ttatagaagt    600
tttgaattgg caatggtcaa tattgtagaa acattatcac tgcgttatgg aagtacaatt    660
gatggctggt ggtttgatca ttcaggtttt ggtgacagtg aattacttca tgctgcggct    720
ctagctggaa ataatgatgc ggcagtagcc tttaatgaag gcgataaagt tcctttggta    780
aataacccag agacattaga cgattacacc tttggtcatc aaacacctat aggtagtgag    840
gtttcttctg atgataaaaa cctacctatg ttaacgtcta tagaagctac tttagatggt    900
attttaactg gttcaggtga tgatgtaggc tctgtgggac atatgtttat gccacttcaa    960
gaaagttgga atggtggcac tgttgtatt tctgaagcga aaggatctga ctggcttaat    1020
cgagcattaa aagccggagg tgcatttaca tgggcactaa gccaagacag taatgatgag   1080
ttaggtggtg gcggagcaag attaatttca gaaccgcagg taaaaatgct tgaacgtatg   1140
agttttaata taggtaaaca attacatatg aatctagatg gttcagatgg tgatactgct   1200
tatgatgact ccgtcaacca atataccgct actgtaaacg gtgctaattt tgttgatgat   1260
gttacaagag gaaagttgc aagtttact gaagacgacc agttagaact agacaattat    1320
caaggtattt caggtggaaa tgcgcgtaca accatggctt ggataaaaac ttcagacagc   1380
aaaggcgata ttattgattg gggtaataac acaacaagcg aacgttggtg gttacgttta   1440
gttgacggta aatttaaact gatattaaaa ggtcctaatc ttacaggaac tacaacactt   1500
aatgacgacc aatggcacca tattgctgtt gtagcttctg ataacgtagt tgctaatatc   1560
aaagtataca ttgatggtgt tttagaaact gttgctgtaa atgacaatgc ttcaactacc   1620
ttcgatacaa ccttaggtgg caatatacaa ataggtgggg cctacaccgg acttatcgat   1680
aaagtgcttg tgcatgatag agcattagat gaaagcgaga ttgagtatgt tgttaattca   1740
tccaatgctg atcttgattt agaggttgca ttagatgtgc gttttgaaga gtcagcaaac   1800
```

-continued

```
tcaactaaag taaccgataa ttctatatat ggacgtcatg gcacaaatcg aggtgctatt    1860
actggcgtgt ttgatgcaga acgtaacagc aatgtgtact cacttgatgg tgttgatagt    1920
ggcgaagata taaatgattt aaaagatagc gactacgaac atgaagttgt aatgacaaca    1980
gataattcta aagactcaaa aggttatagt ggagttaatg gtgcaggtcc gcgtactgta    2040
atggcatgga taaaaacaac ttttggcggt gctgttattg cccaatgggg taataaaaat    2100
tcagttgatg gcgaacaata tgaagttcgt ttaaaaaatg gtgcactgag attagatatt    2160
acaggtggca ttattaaagg cacaacatca attaatgatg gcgagtggca tcatattgct    2220
gtggtttcac ctgatgaaca gttagctaat actaaattgt atgttgatgg tgtactagaa    2280
acagcaacca cttcgggttc tcaagcaacg attgatacta aaactcttaa tggcgatagc    2340
aaagacgtaa taattggtag tacgtttgtt ggcgagatgg acgattttat tattcatcaa    2400
cgcgctttaa gacagtttga agtgaaaaac tcagcaggac tc                       2442
```

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: primer
      CSA+1RLAC

<400> SEQUENCE: 11

```
cgctagcaca tcaaattgtt atccgctcac aatttgatgt gcattaagcc acgca         55
```

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer
      CSA+20FN

<400> SEQUENCE: 12

```
ggccgctagc attaaagcag tgtagtaagg c                                   31
```

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: primer
      CSA70R

<400> SEQUENCE: 13

```
gagaattcag gctggttacg ttacc                                          25
```

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: primer
      CSA+27NF1

<400> SEQUENCE: 14

```
ggccgctagc gcatatccag tgtagtaagg caag                                34
```

<210> SEQ ID NO 15
<211> LENGTH: 24
<212> TYPE: DNA
<213> ORGANISM: Artificial Sequence

```
<220> FEATURE:
<223> OTHER INFORMATION: Description of Artificial Sequence: primer D3F

<400> SEQUENCE: 15
tcaagagcct ttaacgcttc aaaa                                          24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer D3R

<400> SEQUENCE: 16
taaaggctct tgaagggact t                                             21

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: primer
      CSA-ter-FHX

<400> SEQUENCE: 17
gggaagcttt ctagataggt aatctctgct taaaagcac                          39

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: primer
      CSA-ter-R

<400> SEQUENCE: 18
ccagggcctg cgcattctca ttgcaccc                                      28

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: synthetic
      oligonucleotide KS-linker1

<400> SEQUENCE: 19
ccggggatcc g                                                        11

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide KS-linker2

<400> SEQUENCE: 20
tcgacggatc cccgggtac                                                19

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: primer
      CSA1NC-F
```

```
<400> SEQUENCE: 21
aatacaccat ggccggtaaa atg                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: primer
      CSA1NC-R

<400> SEQUENCE: 22
tttaccggcc atggtgtatt acc                                              23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: primer
      CSA13R3

<400> SEQUENCE: 23
ggaattccgt tgaaccattt tacg                                             24

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: primer
      CSA1ND-F

<400> SEQUENCE: 24
aataccatat gtccggtaaa atg                                              23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: primer
      CSA1ND-R

<400> SEQUENCE: 25
tttaccggac atatggtatt acc                                              23

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: synthetic
      oligonucleotide DB-3

<400> SEQUENCE: 26
catgaatcac aaagtgcatc atcatcatca tcatatcgaa ggtagg                     46

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: synthetic
      oligonucleotide DB-4
```

-continued

```
<400> SEQUENCE: 27
aattcctacc ttcgatatga tgatgatgat gatgcactt  gtgatt                    46

<210> SEQ ID NO 28
<211> LENGTH: 15
<212> TYPE: DNA
<213> ORGANISM: Escherichia coli

<400> SEQUENCE: 28
atgaatcaca aagtg                                                      15
```